US012557846B2

(12) United States Patent
Fraser et al.

(10) Patent No.: US 12,557,846 B2
(45) **Date of Patent: *Feb. 24, 2026**

(54) ELECTRONIC VAPOUR PROVISION SYSTEM

(71) Applicant: Nicoventures Trading Limited, London (GB)

(72) Inventors: Rory Fraser, London (GB); Colin Dickens, London (GB); Siddhartha Jain, London (GB)

(73) Assignee: Nicoventures Trading Limited, London (GB)

( * ) Notice: Subject to any disclaimer, the term of this patent is extended or adjusted under 35 U.S.C. 154(b) by 62 days.

This patent is subject to a terminal disclaimer.

(21) Appl. No.: 18/439,178

(22) Filed: Feb. 12, 2024

(65) Prior Publication Data

US 2024/0306718 A1 Sep. 19, 2024

Related U.S. Application Data

(63) Continuation of application No. 15/739,045, filed as application No. PCT/GB2016/051767 on Jun. 15, 2016, now Pat. No. 12,070,070.

(30) Foreign Application Priority Data

Jun. 29, 2015 (GB) ..................................... 1511361

(51) Int. Cl.
*A24F 40/465* (2020.01)
*A24B 15/167* (2020.01)
(Continued)

(52) U.S. Cl.
CPC .......... *A24F 40/465* (2020.01); *A24B 15/167* (2016.11); *A24F 40/485* (2020.01);
(Continued)

(58) Field of Classification Search
None
See application file for complete search history.

(56) References Cited

U.S. PATENT DOCUMENTS 844,272 A 2/1907 Fate
912,986 A 2/1909 Aschenbrenner
(Continued)

FOREIGN PATENT DOCUMENTS

AT 507187 B1 3/2010
AT 508244 A4 12/2010
(Continued)

OTHER PUBLICATIONS

Australian Examination Report for AU Application No. 2016313708, dated Nov. 1, 2019, 7 pages.
(Continued)

*Primary Examiner* — Phu H Nguyen
(74) *Attorney, Agent, or Firm* — MERCHANT & GOULD P.C.—BAT

(57) ABSTRACT

Embodiments of an electronic vapor provision system having a longitudinal axis are disclosed. The electronic vapor provision system includes a control unit and at least one cartridge configured to engage with and disengage from the control unit substantially along the longitudinal axis. The at least one cartridge includes a reservoir of liquid to be vaporized. The electronic vapor provision system further includes an induction heating assembly including at least one drive coil and a plurality of heater elements. The heaters elements are located in the at least one cartridge for vaporizing the liquid. The at least one cartridge is configured to feed liquid from the reservoir onto the heater elements for vaporization. The at least one cartridge is located, when engaged with the control unit, such that the heater elements are within the at least one drive coil. The electronic vapor provision system is configured to support selective energi-
(Continued)

zation of different heater elements from the plurality of heater elements.

18 Claims, 6 Drawing Sheets

(51) Int. Cl.

| | |
|---|---|
| A24F 40/10 | (2020.01) |
| A24F 40/30 | (2020.01) |
| A24F 40/40 | (2020.01) |
| A24F 40/485 | (2020.01) |
| A24F 40/50 | (2020.01) |
| A61M 11/04 | (2006.01) |
| A61M 15/06 | (2006.01) |

(52) U.S. Cl.

CPC ........... *A24F 40/50* (2020.01); *A61M 11/042* (2014.02); *A61M 15/06* (2013.01); *A24F 40/10* (2020.01); *A24F 40/30* (2020.01); *A24F 40/40* (2020.01); *A61M 2205/8206* (2013.01)

(56) References Cited

U.S. PATENT DOCUMENTS

| | | |
|---|---|---|
| 1,071,817 A | 9/1913 | Stanley |
| 1,771,366 A | 7/1930 | Wyss et al. |
| 1,886,391 A | 11/1932 | Henri |
| 2,057,353 A | 10/1936 | Whittemore, Jr. |
| 2,104,266 A | 1/1938 | Mccormick |
| 2,473,325 A | 6/1949 | Aufiero |
| 2,809,634 A | 10/1957 | Hirotada |
| 2,860,638 A | 11/1958 | Frank |
| 3,111,396 A | 11/1963 | Ball |
| 3,144,174 A | 8/1964 | Henry |
| 3,225,954 A | 12/1965 | Herrick et al. |
| 3,265,236 A | 8/1966 | Norman et al. |
| 3,402,724 A | 9/1968 | Blount et al. |
| 3,431,393 A | 3/1969 | Katsuda |
| 3,433,632 A | 3/1969 | Elbert et al. |
| 3,521,643 A | 7/1970 | Toth |
| 3,604,428 A | 9/1971 | Moukaddem |
| 3,804,100 A | 4/1974 | Fariello |
| 3,805,806 A | 4/1974 | Grihalva |
| 3,889,690 A | 6/1975 | Guarnieri |
| 3,964,902 A | 6/1976 | Fletcher et al. |
| 4,009,713 A | 3/1977 | Simmons et al. |
| 4,031,906 A | 6/1977 | Knapp |
| 4,094,119 A | 6/1978 | Sullivan |
| 4,145,001 A | 3/1979 | Weyenberg et al. |
| 4,161,283 A | 7/1979 | Hyman |
| 4,171,000 A | 10/1979 | Uhle |
| 4,193,513 A | 3/1980 | Bull |
| 4,303,083 A | 12/1981 | Burruss, Jr. |
| 4,412,930 A | 11/1983 | Koike et al. |
| 4,427,123 A | 1/1984 | Komeda et al. |
| 4,474,191 A | 10/1984 | Steiner |
| 4,503,851 A | 3/1985 | Braunroth |
| 4,588,976 A | 5/1986 | Jaselli |
| 4,628,187 A | 12/1986 | Sekiguchi et al. |
| 4,638,820 A | 1/1987 | Roberts et al. |
| 4,675,508 A | 6/1987 | Miyaji et al. |
| 4,676,237 A | 6/1987 | Wood et al. |
| 4,677,992 A | 7/1987 | Bliznak |
| 4,694,841 A | 9/1987 | Esparza |
| 4,734,097 A | 3/1988 | Tanabe et al. |
| 4,735,217 A | 4/1988 | Gerth et al. |
| 4,756,318 A | 7/1988 | Clearman et al. |
| 4,765,347 A | 8/1988 | Sensabaugh et al. |
| 4,830,028 A | 5/1989 | Lawson et al. |
| 4,848,374 A | 7/1989 | Chard et al. |
| 4,885,129 A | 12/1989 | Leonard et al. |
| 4,892,109 A | 1/1990 | Strubel |
| 4,907,606 A | 3/1990 | Lilja et al. |
| 4,917,301 A | 4/1990 | Munteanu |
| 4,922,901 A | 5/1990 | Brooks et al. |
| 4,944,317 A | 7/1990 | Thal |
| 4,945,929 A | 8/1990 | Egilmex |
| 4,945,931 A | 8/1990 | Gori |
| 4,947,874 A | 8/1990 | Brooks et al. |
| 4,947,875 A | 8/1990 | Brooks et al. |
| 4,978,814 A | 12/1990 | Honour |
| 5,027,837 A | 7/1991 | Clearman et al. |
| 5,040,551 A | 8/1991 | Schlatter et al. |
| 5,046,514 A | 9/1991 | Bolt |
| 5,060,671 A | 10/1991 | Counts et al. |
| 5,093,894 A | 3/1992 | Deevi et al. |
| 5,095,647 A | 3/1992 | Zobele et al. |
| 5,095,921 A | 3/1992 | Losee et al. |
| 5,096,921 A | 3/1992 | Bollinger et al. |
| 5,099,861 A | 3/1992 | Clearman et al. |
| 5,121,881 A | 6/1992 | Lembeck |
| 5,143,048 A | 9/1992 | Cheney, III |
| 5,144,962 A | 9/1992 | Counts et al. |
| 5,167,242 A | 12/1992 | Turner et al. |
| 5,179,966 A | 1/1993 | Losee et al. |
| 5,190,060 A | 3/1993 | Gerding et al. |
| 5,203,355 A | 4/1993 | Clearman et al. |
| 5,224,498 A | 7/1993 | Deevi et al. |
| 5,247,947 A | 9/1993 | Clearman et al. |
| 5,249,586 A | 10/1993 | Morgan et al. |
| 5,251,688 A | 10/1993 | Schatz |
| 5,261,424 A | 11/1993 | Sprinkel, Jr. |
| 5,269,327 A | 12/1993 | Counts et al. |
| 5,271,980 A | 12/1993 | Bell |
| 5,285,798 A | 2/1994 | Banerjee et al. |
| 5,303,720 A | 4/1994 | Banerjee et al. |
| 5,305,733 A | 4/1994 | Walters |
| 5,322,075 A | 6/1994 | Deevi et al. |
| 5,327,915 A | 7/1994 | Porenski et al. |
| 5,331,979 A | 7/1994 | Henley |
| 5,345,951 A | 9/1994 | Serrano et al. |
| 5,353,813 A | 10/1994 | Deevi et al. |
| 5,369,249 A | 11/1994 | Kwon |
| 5,369,723 A | 11/1994 | Counts et al. |
| 5,372,148 A | 12/1994 | Mccafferty et al. |
| 5,388,574 A | 2/1995 | Ingebrethsen |
| 5,388,594 A | 2/1995 | Counts et al. |
| 5,390,864 A | 2/1995 | Alexander |
| 5,402,803 A | 4/1995 | Takagi |
| 5,408,574 A | 4/1995 | Deevi et al. |
| 5,468,936 A | 11/1995 | Deevi et al. |
| 5,479,948 A | 1/1996 | Counts et al. |
| 5,497,792 A | 3/1996 | Prasad et al. |
| 5,501,236 A | 3/1996 | Hill et al. |
| 5,505,214 A | 4/1996 | Collins et al. |
| 5,534,020 A | 7/1996 | Cheney et al. |
| 5,540,241 A | 7/1996 | Kim |
| 5,553,791 A | 9/1996 | Alexander |
| 5,573,140 A | 11/1996 | Satomi et al. |
| 5,613,504 A | 3/1997 | Collins et al. |
| 5,613,505 A | 3/1997 | Campbell et al. |
| 5,636,787 A | 6/1997 | Gowhari |
| 5,649,554 A | 7/1997 | Sprinkel et al. |
| 5,665,262 A | 9/1997 | Hajaligol et al. |
| 5,666,977 A | 9/1997 | Higgins et al. |
| 5,692,291 A | 12/1997 | Deevi et al. |
| 5,726,421 A | 3/1998 | Fleischhauer et al. |
| 5,742,251 A | 4/1998 | Gerber |
| 5,743,251 A | 4/1998 | Howell et al. |
| 5,771,845 A | 6/1998 | Pistien et al. |
| 5,798,154 A | 8/1998 | Bryan |
| 5,865,185 A | 2/1999 | Collins et al. |
| 5,865,186 A | 2/1999 | Volsey, II |
| 5,984,953 A | 11/1999 | Sabin et al. |
| 6,026,820 A | 2/2000 | Baggett et al. |
| 6,037,568 A | 3/2000 | Hatanaka et al. |
| 6,040,560 A | 3/2000 | Fleischhauer et al. |
| 6,053,176 A | 4/2000 | Adams et al. |
| 6,058,711 A | 5/2000 | Maciaszek et al. |
| 6,089,857 A | 7/2000 | Matsuura et al. |
| 6,095,505 A | 8/2000 | Miller |
| 6,116,231 A | 9/2000 | Sabin et al. |

(56)  References Cited

U.S. PATENT DOCUMENTS

| | | |
|---|---|---|
| 6,125,853 A | 10/2000 | Susa et al. |
| 6,155,268 A | 12/2000 | Takeuchi |
| 6,224,179 B1 | 5/2001 | Wenning et al. |
| 6,275,650 B1 | 8/2001 | Lambert |
| 6,289,889 B1 | 9/2001 | Bell et al. |
| 6,315,366 B1 | 11/2001 | Post et al. |
| 6,376,816 B2 | 4/2002 | Cooper et al. |
| 6,644,383 B2 | 11/2003 | Joseph et al. |
| 6,652,804 B1 | 11/2003 | Neumann et al. |
| 6,681,998 B2 | 1/2004 | Sharpe et al. |
| 6,701,921 B2 | 3/2004 | Sprinkel et al. |
| 6,723,115 B1 | 4/2004 | Daly |
| 6,790,496 B1 | 9/2004 | Levander et al. |
| 6,803,550 B2 | 10/2004 | Sharpe et al. |
| 6,827,080 B2 | 12/2004 | Fish et al. |
| 6,868,230 B2 | 3/2005 | Gerhardinger |
| 6,953,474 B2 | 10/2005 | Lu |
| 6,994,096 B2 | 2/2006 | Rostami et al. |
| 7,100,618 B2 | 9/2006 | Dominguez |
| 7,112,712 B1 | 9/2006 | Ancell |
| 7,185,659 B2 | 3/2007 | Sharpe |
| 7,263,282 B2 | 8/2007 | Meyer |
| 7,374,063 B2 | 5/2008 | Reid |
| 7,400,940 B2 | 7/2008 | Mcrae et al. |
| 7,540,286 B2 | 6/2009 | Cross et al. |
| 7,624,739 B2 | 12/2009 | Snaidr et al. |
| 7,726,320 B2 | 6/2010 | Robinson et al. |
| 7,767,698 B2 | 8/2010 | Warchol et al. |
| 7,832,410 B2 | 11/2010 | Hon |
| 7,913,688 B2 | 3/2011 | Cross et al. |
| 7,992,554 B2 | 8/2011 | Radomski et al. |
| 8,061,361 B2 | 11/2011 | Maeder et al. |
| 8,079,371 B2 | 12/2011 | Robinson et al. |
| 8,081,474 B1 | 12/2011 | Zohni et al. |
| 8,118,021 B2 | 2/2012 | Cho et al. |
| 8,375,957 B2 | 2/2013 | Hon |
| 8,393,331 B2 | 3/2013 | Hon |
| 8,430,106 B2 | 4/2013 | Potter et al. |
| 8,459,271 B2 | 6/2013 | Inagaki |
| 8,490,628 B2 | 7/2013 | Hon |
| 8,511,318 B2 | 8/2013 | Hon |
| 8,678,013 B2 | 3/2014 | Crooks et al. |
| 8,689,805 B2 | 4/2014 | Hon |
| 8,752,545 B2 | 6/2014 | Buchberger |
| 8,757,404 B1 | 6/2014 | Fleckenstein |
| 8,807,140 B1 | 8/2014 | Scatterday |
| 8,833,364 B2 | 9/2014 | Buchberger |
| 8,897,628 B2 | 11/2014 | Conley et al. |
| 8,899,238 B2 | 12/2014 | Robinson et al. |
| 8,910,641 B2 | 12/2014 | Hon |
| 8,948,578 B2 | 2/2015 | Buchberger |
| 9,357,803 B2 | 6/2016 | Egoyants et al. |
| 9,414,619 B2 | 8/2016 | Sizer et al. |
| 9,414,629 B2 | 8/2016 | Egoyants et al. |
| 9,554,598 B2 | 1/2017 | Egoyants et al. |
| 9,609,894 B2 | 4/2017 | Abramov et al. |
| 9,623,205 B2 | 4/2017 | Buchberger |
| 9,693,587 B2 | 7/2017 | Plojoux et al. |
| 9,814,269 B2 | 11/2017 | Li et al. |
| 9,820,512 B2 | 11/2017 | Mironov et al. |
| 9,980,523 B2 | 5/2018 | Abramov et al. |
| 9,999,256 B2 | 6/2018 | Abramov et al. |
| 10,010,695 B2 | 7/2018 | Buchberger |
| 10,015,986 B2 | 7/2018 | Cadieux et al. |
| 10,045,562 B2 | 8/2018 | Buchberger |
| 10,070,668 B2 | 9/2018 | Li et al. |
| 10,219,543 B2 | 3/2019 | Gill et al. |
| 10,327,473 B2 | 6/2019 | Mironov |
| 10,856,575 B2 | 12/2020 | Gill et al. |
| 2001/0042546 A1 | 11/2001 | Umeda et al. |
| 2002/0005207 A1 | 1/2002 | Wrenn et al. |
| 2002/0016370 A1 | 2/2002 | Shytle et al. |
| 2002/0078951 A1 | 6/2002 | Nichols et al. |
| 2002/0078956 A1 | 6/2002 | Sharpe et al. |
| 2002/0079309 A1 | 6/2002 | Cox et al. |
| 2002/0079377 A1 | 6/2002 | Nichols |
| 2003/0005620 A1 | 1/2003 | Ananth et al. |
| 2003/0007887 A1 | 1/2003 | Roumpos et al. |
| 2003/0033055 A1 | 2/2003 | Mcrae et al. |
| 2003/0049025 A1 | 3/2003 | Neumann et al. |
| 2003/0079309 A1 | 5/2003 | Vandenbelt et al. |
| 2003/0102304 A1 | 6/2003 | Boyers |
| 2003/0106552 A1 | 6/2003 | Sprinkel et al. |
| 2003/0108342 A1 | 6/2003 | Sherwood et al. |
| 2003/0136404 A1 | 7/2003 | Hindle et al. |
| 2003/0146224 A1 | 8/2003 | Fujii et al. |
| 2003/0200964 A1 | 10/2003 | Blakley et al. |
| 2003/0202169 A1 | 10/2003 | Liu |
| 2003/0230567 A1 | 12/2003 | Centanni et al. |
| 2004/0003820 A1 | 1/2004 | Iannuzzi |
| 2004/0031485 A1 | 2/2004 | Rustad et al. |
| 2004/0079368 A1 | 4/2004 | Gupta et al. |
| 2004/0096204 A1 | 5/2004 | Gerhardinger |
| 2004/0129793 A1 | 7/2004 | Nguyen et al. |
| 2004/0149296 A1 | 8/2004 | Rostami et al. |
| 2004/0149297 A1 | 8/2004 | Sharpe |
| 2004/0149737 A1 | 8/2004 | Sharpe et al. |
| 2004/0210151 A1 | 10/2004 | Tsukashima et al. |
| 2004/0223917 A1 | 11/2004 | Hindle et al. |
| 2004/0226568 A1 | 11/2004 | Takeuchi et al. |
| 2005/0025213 A1 | 2/2005 | Parks |
| 2005/0063686 A1 | 3/2005 | Whittle et al. |
| 2005/0145260 A1 | 7/2005 | Inagaki et al. |
| 2005/0194013 A1 | 9/2005 | Wright |
| 2005/0204799 A1 | 9/2005 | Koch |
| 2005/0211711 A1 | 9/2005 | Reid |
| 2005/0268911 A1 | 12/2005 | Cross et al. |
| 2006/0078477 A1 | 4/2006 | Althouse et al. |
| 2006/0137681 A1 | 6/2006 | Von et al. |
| 2007/0014549 A1 | 1/2007 | Demarest et al. |
| 2007/0045288 A1 | 3/2007 | Nelson |
| 2007/0062548 A1 | 3/2007 | Horstmann et al. |
| 2007/0074734 A1 | 4/2007 | Braunshteyn et al. |
| 2007/0102013 A1 | 5/2007 | Adams et al. |
| 2007/0107879 A1 | 5/2007 | Radomski et al. |
| 2007/0155255 A1 | 7/2007 | Galauner et al. |
| 2007/0204858 A1 | 9/2007 | Abelbeck |
| 2007/0204868 A1 | 9/2007 | Bollinger et al. |
| 2007/0267409 A1 | 11/2007 | Gard et al. |
| 2007/0283972 A1 | 12/2007 | Monsees et al. |
| 2008/0085139 A1 | 4/2008 | Roof |
| 2008/0092912 A1 | 4/2008 | Robinson et al. |
| 2008/0149118 A1 | 6/2008 | Oglesby et al. |
| 2008/0156326 A1 | 7/2008 | Belcastro et al. |
| 2008/0216828 A1 | 9/2008 | Wensley et al. |
| 2008/0233318 A1 | 9/2008 | Coyle |
| 2008/0241255 A1 | 10/2008 | Rose et al. |
| 2008/0302374 A1 | 12/2008 | Wengert et al. |
| 2009/0032034 A1 | 2/2009 | Steinberg |
| 2009/0056728 A1 | 3/2009 | Baker |
| 2009/0065011 A1 | 3/2009 | Maeder et al. |
| 2009/0090472 A1 | 4/2009 | Radomski |
| 2009/0095311 A1 | 4/2009 | Han |
| 2009/0120928 A1 | 5/2009 | Lee et al. |
| 2009/0126745 A1 | 5/2009 | Hon |
| 2009/0151717 A1 | 6/2009 | Bowen et al. |
| 2009/0188490 A1 | 7/2009 | Han |
| 2009/0230117 A1 | 9/2009 | Fernando et al. |
| 2009/0241947 A1 | 10/2009 | Bedini et al. |
| 2009/0260641 A1 | 10/2009 | Monsees et al. |
| 2009/0272379 A1 | 11/2009 | Thorens et al. |
| 2009/0293892 A1 | 12/2009 | Williams et al. |
| 2009/0304372 A1 | 12/2009 | Gubler et al. |
| 2009/0320863 A1 | 12/2009 | Fernando et al. |
| 2010/0024834 A1 | 2/2010 | Oglesby et al. |
| 2010/0059070 A1 | 3/2010 | Potter et al. |
| 2010/0065653 A1 | 3/2010 | Wingo et al. |
| 2010/0083959 A1 | 4/2010 | Siller |
| 2010/0108059 A1 | 5/2010 | Axelsson et al. |
| 2010/0126516 A1 | 5/2010 | Yomtov et al. |
| 2010/0163063 A1 | 7/2010 | Fernando et al. |
| 2010/0200006 A1 | 8/2010 | Robinson et al. |
| 2010/0236546 A1 | 9/2010 | Yamada et al. |
| 2010/0242974 A1 | 9/2010 | Pan |

(56)                    References Cited

U.S. PATENT DOCUMENTS

| | | | |
|---|---|---|---|
| 2010/0242975 A1 | 9/2010 | Hearn | |
| 2010/0300467 A1 | 12/2010 | Kuistila et al. | |
| 2010/0307518 A1 | 12/2010 | Wang | |
| 2011/0011396 A1 | 1/2011 | Fang | |
| 2011/0036363 A1 | 2/2011 | Urtsev et al. | |
| 2011/0090266 A1 | 4/2011 | King et al. | |
| 2011/0094523 A1 | 4/2011 | Thorens et al. | |
| 2011/0126848 A1 | 6/2011 | Zuber et al. | |
| 2011/0155153 A1 | 6/2011 | Thorens et al. | |
| 2011/0155718 A1* | 6/2011 | Greim | H05B 3/46 |
| | | | 219/539 |
| 2011/0192914 A1 | 8/2011 | Ishigami | |
| 2011/0226236 A1 | 9/2011 | Buchberger | |
| 2011/0236002 A1 | 9/2011 | Oglesby et al. | |
| 2011/0240022 A1 | 10/2011 | Hodges et al. | |
| 2011/0264084 A1 | 10/2011 | Reid | |
| 2011/0277757 A1 | 11/2011 | Terry et al. | |
| 2011/0290266 A1 | 12/2011 | Koeller | |
| 2011/0290267 A1 | 12/2011 | Yamada et al. | |
| 2011/0297166 A1 | 12/2011 | Takeuchi et al. | |
| 2011/0303231 A1 | 12/2011 | Li et al. | |
| 2012/0006342 A1 | 1/2012 | Rose et al. | |
| 2012/0132196 A1 | 5/2012 | Vladyslavovych | |
| 2012/0145169 A1 | 6/2012 | Wu | |
| 2012/0214926 A1 | 8/2012 | Berthold et al. | |
| 2012/0234315 A1 | 9/2012 | Li et al. | |
| 2012/0234821 A1 | 9/2012 | Shimizu | |
| 2012/0255546 A1 | 10/2012 | Goetz et al. | |
| 2012/0260927 A1 | 10/2012 | Liu | |
| 2012/0285476 A1 | 11/2012 | Hon | |
| 2012/0305545 A1 | 12/2012 | Brosnan et al. | |
| 2012/0318882 A1 | 12/2012 | Abehasera | |
| 2013/0030125 A1 | 1/2013 | Buryak et al. | |
| 2013/0074857 A1 | 3/2013 | Buchberger | |
| 2013/0081623 A1 | 4/2013 | Buchberger | |
| 2013/0087160 A1 | 4/2013 | Gherghe | |
| 2013/0133675 A1 | 5/2013 | Shinozaki et al. | |
| 2013/0142782 A1 | 6/2013 | Rahmel et al. | |
| 2013/0146588 A1 | 6/2013 | Child | |
| 2013/0192615 A1 | 8/2013 | Tucker et al. | |
| 2013/0213419 A1 | 8/2013 | Tucker et al. | |
| 2013/0220315 A1 | 8/2013 | Conley et al. | |
| 2013/0264335 A1 | 10/2013 | Uchida | |
| 2013/0284192 A1 | 10/2013 | Peleg et al. | |
| 2013/0300350 A1 | 11/2013 | Xiang | |
| 2013/0306064 A1 | 11/2013 | Thorens et al. | |
| 2013/0306065 A1 | 11/2013 | Thorens et al. | |
| 2013/0306084 A1 | 11/2013 | Flick | |
| 2013/0319435 A1 | 12/2013 | Flick | |
| 2013/0333700 A1 | 12/2013 | Buchberger | |
| 2013/0340750 A1 | 12/2013 | Thorens et al. | |
| 2013/0340779 A1 | 12/2013 | Liu | |
| 2014/0000638 A1 | 1/2014 | Sebastian et al. | |
| 2014/0060528 A1 | 3/2014 | Liu | |
| 2014/0060554 A1 | 3/2014 | Collett et al. | |
| 2014/0060555 A1 | 3/2014 | Chang et al. | |
| 2014/0182608 A1 | 7/2014 | Egoyants et al. | |
| 2014/0182843 A1 | 7/2014 | Vinegar | |
| 2014/0186015 A1 | 7/2014 | Breiwa et al. | |
| 2014/0202454 A1 | 7/2014 | Buchberger | |
| 2014/0202476 A1 | 7/2014 | Egoyants et al. | |
| 2014/0209105 A1 | 7/2014 | Sears et al. | |
| 2014/0216485 A1 | 8/2014 | Egoyants et al. | |
| 2014/0238396 A1 | 8/2014 | Buchberger | |
| 2014/0238423 A1 | 8/2014 | Tucker et al. | |
| 2014/0238424 A1 | 8/2014 | Macko et al. | |
| 2014/0261490 A1 | 9/2014 | Kane | |
| 2014/0270726 A1 | 9/2014 | Egoyants et al. | |
| 2014/0270730 A1 | 9/2014 | Depiano et al. | |
| 2014/0278250 A1 | 9/2014 | Smith et al. | |
| 2014/0283825 A1 | 9/2014 | Buchberger | |
| 2014/0286630 A1 | 9/2014 | Buchberger | |
| 2014/0299125 A1 | 10/2014 | Buchberger | |
| 2014/0299141 A1 | 10/2014 | Flick | |
| 2014/0301721 A1 | 10/2014 | Ruscio et al. | |
| 2014/0305449 A1 | 10/2014 | Plojoux et al. | |
| 2014/0305454 A1 | 10/2014 | Rinker et al. | |
| 2014/0326257 A1 | 11/2014 | Jalloul et al. | |
| 2014/0334802 A1 | 11/2014 | Dubief | |
| 2014/0338680 A1 | 11/2014 | Abramov et al. | |
| 2014/0338686 A1 | 11/2014 | Plojoux et al. | |
| 2014/0345606 A1 | 11/2014 | Talon | |
| 2014/0346689 A1 | 11/2014 | Dubief | |
| 2014/0360515 A1 | 12/2014 | Vasiliev et al. | |
| 2014/0360516 A1 | 12/2014 | Liu | |
| 2014/0366898 A1 | 12/2014 | Monsees et al. | |
| 2015/0040925 A1 | 2/2015 | Saleem et al. | |
| 2015/0068541 A1 | 3/2015 | Sears et al. | |
| 2015/0114409 A1 | 4/2015 | Brammer et al. | |
| 2015/0114411 A1 | 4/2015 | Buchberger | |
| 2015/0128967 A1 | 5/2015 | Robinson et al. | |
| 2015/0142088 A1 | 5/2015 | Riva Godoy | |
| 2015/0157055 A1 | 6/2015 | Lord | |
| 2015/0196058 A1 | 7/2015 | Lord | |
| 2015/0208728 A1 | 7/2015 | Lord | |
| 2015/0216237 A1 | 8/2015 | Wensley et al. | |
| 2015/0223520 A1 | 8/2015 | Phillips et al. | |
| 2015/0245669 A1 | 9/2015 | Cadieux et al. | |
| 2015/0272219 A1 | 10/2015 | Hatrick et al. | |
| 2015/0272222 A1 | 10/2015 | Spinka et al. | |
| 2015/0335062 A1 | 11/2015 | Shinkawa et al. | |
| 2016/0003403 A1 | 1/2016 | Smith | |
| 2016/0021934 A1 | 1/2016 | Cadieux et al. | |
| 2016/0073693 A1 | 3/2016 | Reevell | |
| 2016/0106154 A1 | 4/2016 | Lord | |
| 2016/0106155 A1 | 4/2016 | Reevell | |
| 2016/0120221 A1 | 5/2016 | Mironov et al. | |
| 2016/0146506 A1 | 5/2016 | Brereton et al. | |
| 2016/0168438 A1 | 6/2016 | Harding et al. | |
| 2016/0255879 A1 | 9/2016 | Paprocki et al. | |
| 2016/0295921 A1 | 10/2016 | Mironov et al. | |
| 2017/0006916 A1 | 1/2017 | Liu | |
| 2017/0027233 A1 | 2/2017 | Mironov | |
| 2017/0042245 A1 | 2/2017 | Buchberger et al. | |
| 2017/0055574 A1 | 3/2017 | Kaufman et al. | |
| 2017/0055575 A1 | 3/2017 | Wilke et al. | |
| 2017/0055580 A1 | 3/2017 | Blandino et al. | |
| 2017/0055581 A1 | 3/2017 | Wilke et al. | |
| 2017/0055582 A1 | 3/2017 | Blandino et al. | |
| 2017/0055583 A1 | 3/2017 | Blandino et al. | |
| 2017/0055584 A1 | 3/2017 | Blandino et al. | |
| 2017/0055585 A1 | 3/2017 | Fursa et al. | |
| 2017/0064996 A1 | 3/2017 | Mironov | |
| 2017/0071250 A1 | 3/2017 | Mironov et al. | |
| 2017/0079325 A1 | 3/2017 | Mironov | |
| 2017/0079330 A1 | 3/2017 | Mironov et al. | |
| 2017/0095006 A1 | 4/2017 | Egoyants et al. | |
| 2017/0105452 A1 | 4/2017 | Mironov et al. | |
| 2017/0119046 A1 | 5/2017 | Kaufman et al. | |
| 2017/0119047 A1 | 5/2017 | Blandino et al. | |
| 2017/0119048 A1 | 5/2017 | Kaufman et al. | |
| 2017/0119049 A1 | 5/2017 | Blandino et al. | |
| 2017/0119050 A1 | 5/2017 | Blandino et al. | |
| 2017/0119051 A1 | 5/2017 | Blandino et al. | |
| 2017/0156403 A1 | 6/2017 | Gill et al. | |
| 2017/0156406 A1 | 6/2017 | Abramov et al. | |
| 2017/0156407 A1 | 6/2017 | Abramov et al. | |
| 2017/0174418 A1 | 6/2017 | Cai | |
| 2017/0196273 A1 | 7/2017 | Qiu | |
| 2017/0197043 A1 | 7/2017 | Buchberger | |
| 2017/0197044 A1 | 7/2017 | Buchberger | |
| 2017/0197046 A1 | 7/2017 | Buchberger | |
| 2017/0197048 A1 | 7/2017 | Khosrowshahi et al. | |
| 2017/0197049 A1 | 7/2017 | Doll | |
| 2017/0197050 A1 | 7/2017 | Reinburg et al. | |
| 2017/0199048 A1 | 7/2017 | Igumnov et al. | |
| 2017/0231276 A1 | 8/2017 | Mironov et al. | |
| 2017/0231281 A1 | 8/2017 | Hatton et al. | |
| 2017/0303585 A1 | 10/2017 | Florack et al. | |
| 2017/0332700 A1 | 11/2017 | Plews et al. | |
| 2017/0340008 A1 | 11/2017 | Sebastian et al. | |
| 2018/0168227 A1 | 6/2018 | Fraser et al. | |
| 2018/0184712 A1 | 7/2018 | Fraser et al. | |
| 2018/0184713 A1 | 7/2018 | Mironov et al. | |

(56) References Cited

U.S. PATENT DOCUMENTS

| | | |
|---|---|---|
| 2018/0192700 A1 | 7/2018 | Fraser et al. |
| 2018/0235279 A1 | 8/2018 | Wilke et al. |
| 2018/0242633 A1 | 8/2018 | Wilke et al. |
| 2018/0242636 A1 | 8/2018 | Blandino et al. |
| 2018/0271171 A1 | 9/2018 | Abramov et al. |
| 2018/0279677 A1 | 10/2018 | Blandino et al. |
| 2018/0317552 A1 | 11/2018 | Kaufman et al. |
| 2018/0317553 A1 | 11/2018 | Blandino et al. |
| 2018/0317554 A1 | 11/2018 | Kaufman et al. |
| 2018/0317555 A1 | 11/2018 | Blandino et al. |
| 2019/0000142 A1 | 1/2019 | Lavanchy et al. |
| 2019/0014820 A1 | 1/2019 | Malgat |
| 2019/0142068 A1 | 5/2019 | Gill et al. |
| 2019/0182909 A1 | 6/2019 | Fursa et al. |
| 2021/0112863 A1 | 4/2021 | Hon |

FOREIGN PATENT DOCUMENTS

| | | | |
|---|---|---|---|
| AT | 510405 A4 | 4/2012 | |
| AT | 510504 A1 | 4/2012 | |
| AU | 6393173 A | 6/1975 | |
| CA | 2003521 A1 | 5/1990 | |
| CA | 2003522 A1 | 5/1990 | |
| CA | 2309376 A1 | 11/2000 | |
| CA | 2712412 A1 | 12/2009 | |
| CA | 2937722 A1 | 11/2015 | |
| CA | 2974770 A1 | 12/2015 | |
| CA | 2982164 A1 | 10/2016 | |
| CH | 698603 B1 | 9/2009 | |
| CL | 2007002226 A1 | 2/2008 | |
| CL | 2013003637 A1 | 7/2014 | |
| CL | 2014002840 A1 | 12/2014 | |
| CN | 86102917 A | 11/1987 | |
| CN | 1040914 A | 4/1990 | |
| CN | 1045691 A | 10/1990 | |
| CN | 2092880 U | 1/1992 | |
| CN | 2220168 Y | 2/1996 | |
| CN | 1122213 A | 5/1996 | |
| CN | 1126426 A | 7/1996 | |
| CN | 2246744 Y | 2/1997 | |
| CN | 1196660 A | 10/1998 | |
| CN | 1196661 A | 10/1998 | |
| CN | 1205849 A | 1/1999 | |
| CN | 1312730 A | 9/2001 | |
| CN | 1106812 C | 4/2003 | |
| CN | 2598364 Y | 1/2004 | |
| CN | 1578895 A | 2/2005 | |
| CN | 2719043 Y | 8/2005 | |
| CN | 1694765 A | 11/2005 | |
| CN | 1703279 A | 11/2005 | |
| CN | 200966824 Y | 10/2007 | |
| CN | 201076006 Y | 6/2008 | |
| CN | 101238047 A | 8/2008 | |
| CN | 101267749 A | 9/2008 | |
| CN | 101277622 A | 10/2008 | |
| CN | 101277623 A | 10/2008 | |
| CN | 101282660 A | 10/2008 | |
| CN | 201185656 Y | 1/2009 | |
| CN | 101390659 A | 3/2009 | |
| CN | 201199922 Y | 3/2009 | |
| CN | 201238609 Y | 5/2009 | |
| CN | 101500443 A | 8/2009 | |
| CN | 101516425 A | 8/2009 | |
| CN | 101557728 A | 10/2009 | |
| CN | 101606758 A | 12/2009 | |
| CN | 100577043 C | 1/2010 | |
| CN | 201375023 Y | 1/2010 | |
| CN | 101648041 A | 2/2010 | |
| CN | 201445686 U | 5/2010 | |
| CN | 101878958 A | 11/2010 | |
| CN | 101925309 A | 12/2010 | |
| CN | 201762288 U | 3/2011 | |
| CN | 101606758 B | 4/2011 | |
| CN | 102014677 A | 4/2011 | |
| CN | 201869778 U | 6/2011 | |
| CN | 102131411 A | 7/2011 | |
| CN | 202172846 U | 3/2012 | |
| CN | 202233006 U | 5/2012 | |
| CN | 102573968 A | 7/2012 | |
| CN | 102604599 A | 7/2012 | |
| CN | 102655773 A | 9/2012 | |
| CN | 102861694 A | 1/2013 | |
| CN | 202722498 U | 2/2013 | |
| CN | 202750708 U | 2/2013 | |
| CN | 103052380 A | 4/2013 | |
| CN | 103054196 A | 4/2013 | |
| CN | 103359550 A | 10/2013 | |
| CN | 203369385 U | 1/2014 | |
| CN | 203369386 U | 1/2014 | |
| CN | 103596458 A | 2/2014 | |
| CN | 103689812 A | 4/2014 | |
| CN | 103720057 A | 4/2014 | |
| CN | 103783673 A | 5/2014 | |
| CN | 203618786 U | 6/2014 | |
| CN | 103974639 A | 8/2014 | |
| CN | 104000305 A | 8/2014 | |
| CN | 104010534 A | 8/2014 | |
| CN | 203748673 U | 8/2014 | |
| CN | 203762288 U | 8/2014 | |
| CN | 104039033 A | 9/2014 | |
| CN | 104095291 A | 10/2014 | |
| CN | 203952439 U | 11/2014 | |
| CN | 104244750 A | 12/2014 | |
| CN | 203969196 U | 12/2014 | |
| CN | 203986095 U | 12/2014 | |
| CN | 203986113 U | 12/2014 | |
| CN | 204032371 U | 12/2014 | |
| CN | 104256899 A | 1/2015 | |
| CN | 204091003 U | 1/2015 | |
| CN | 204132397 U | 2/2015 | |
| CN | 204146328 U | 2/2015 | |
| CN | 104382238 A | 3/2015 | |
| CN | 104382239 A | 3/2015 | |
| CN | 204217894 U | 3/2015 | |
| CN | 104540404 A | 4/2015 | |
| CN | 204273248 U | 4/2015 | |
| CN | 204317492 U | 5/2015 | |
| CN | 204317506 U | 5/2015 | |
| CN | 104720120 A | 6/2015 | |
| CN | 104720121 A | 6/2015 | |
| CN | 204444245 U | 7/2015 | |
| CN | 105873462 A | 8/2016 | |
| CN | 106102863 A | 11/2016 | |
| CN | 104095291 B | 1/2017 | |
| CN | 106455711 A | 2/2017 | |
| CN | 106455715 A | 2/2017 | |
| CN | 106455711 B | 9/2019 | |
| DE | 1950439 A1 | 4/1971 | |
| DE | 3148335 A1 | 7/1983 | |
| DE | 3218760 A1 | 12/1983 | |
| DE | 3936687 A1 | 5/1990 | |
| DE | 29713866 U1 | 10/1997 | |
| DE | 29719509 U1 | 1/1998 | |
| DE | 19630619 A1 | 2/1998 | |
| DE | 19654945 A1 | 3/1998 | |
| DE | 10330681 B3 | 6/2004 | |
| DE | 202006013439 U1 | 10/2006 | |
| DE | 102005023278 A1 | 11/2006 | |
| DE | 102010046482 A1 | 3/2012 | |
| DE | 202013100606 U1 | 2/2013 | |
| DE | 102013002555 A1 | 6/2014 | |
| EA | 019736 B1 | 5/2014 | |
| EP | 0280262 A2 | 8/1988 | |
| EP | 0295122 A2 | 12/1988 | |
| EP | 0309227 A2 | 3/1989 | |
| EP | 0358002 A2 | 3/1990 | |
| EP | 0358114 A2 | 3/1990 | |
| EP | 0371285 A2 | 6/1990 | |
| EP | 0418464 A2 | 3/1991 | |
| EP | 0430559 A2 | 6/1991 | |
| EP | 0430566 A2 | 6/1991 | |
| EP | 0438862 A2 | 7/1991 | |
| EP | 0444553 A2 | 9/1991 | |
| EP | 0488488 A1 | 6/1992 | |

(56) References Cited

FOREIGN PATENT DOCUMENTS

| | | | |
|---|---|---|---|
| EP | 0491952 | A1 | 7/1992 |
| EP | 0503767 | A1 | 9/1992 |
| EP | 0603613 | A1 | 6/1994 |
| EP | 0703735 | A1 | 4/1996 |
| EP | 0845220 | A1 | 6/1998 |
| EP | 0893071 | A1 | 1/1999 |
| EP | 0703735 | B1 | 7/2001 |
| EP | 1128743 | A1 | 9/2001 |
| EP | 1166814 | A2 | 1/2002 |
| EP | 1166847 | A2 | 1/2002 |
| EP | 1609376 | A1 | 12/2005 |
| EP | 1618803 | A1 | 1/2006 |
| EP | 1454840 | B1 | 9/2006 |
| EP | 1736065 | A1 | 12/2006 |
| EP | 1757921 | A2 | 2/2007 |
| EP | 1940254 | A2 | 7/2008 |
| EP | 2018886 | A1 | 1/2009 |
| EP | 2022349 | A1 | 2/2009 |
| EP | 1357025 | B1 | 7/2009 |
| EP | 2110033 | A1 | 10/2009 |
| EP | 2113178 | A1 | 11/2009 |
| EP | 1947965 | B1 | 2/2010 |
| EP | 2186833 | A1 | 5/2010 |
| EP | 2316286 | A1 | 5/2011 |
| EP | 2327318 | A1 | 6/2011 |
| EP | 2340729 | A1 | 7/2011 |
| EP | 2340730 | A1 | 7/2011 |
| EP | 2394520 | A1 | 12/2011 |
| EP | 2444112 | A1 | 4/2012 |
| EP | 2253541 | B1 | 5/2012 |
| EP | 2520186 | A1 | 11/2012 |
| EP | 2609821 | A1 | 7/2013 |
| EP | 2698070 | A1 | 2/2014 |
| EP | 2762019 | A1 | 8/2014 |
| EP | 2785208 | A1 | 10/2014 |
| EP | 2835062 | A1 | 2/2015 |
| EP | 2907397 | A1 | 8/2015 |
| EP | 2975957 | A1 | 1/2016 |
| EP | 3005890 | A1 | 4/2016 |
| EP | 3062647 | A1 | 9/2016 |
| EP | 3313212 | B1 | 4/2019 |
| EP | 3313214 | B1 | 6/2019 |
| FR | 960469 | A | 4/1950 |
| GB | 25575 | | 3/1912 |
| GB | 191125575 | A | 3/1912 |
| GB | 191126138 | A | 3/1912 |
| GB | 347650 | A | 4/1931 |
| GB | 426247 | A | 3/1935 |
| GB | 1313525 | A | 4/1973 |
| GB | 1511358 | A | 5/1978 |
| GB | 2495923 | A | 5/2013 |
| GB | 2504732 | A | 2/2014 |
| GB | 2504732 | B | 1/2015 |
| GB | 2516924 | A | 2/2015 |
| GB | 2527597 | A | 12/2015 |
| HK | 1196511 | A1 | 12/2014 |
| HK | 1226611 | A | 10/2017 |
| JP | S457120 | Y1 | 4/1970 |
| JP | S5314173 | A | 2/1978 |
| JP | S5752456 | A | 3/1982 |
| JP | S59106340 | A | 6/1984 |
| JP | S6196763 | A | 5/1986 |
| JP | S6196765 | A | 5/1986 |
| JP | S62501050 | A | 4/1987 |
| JP | S62205184 | A | 9/1987 |
| JP | S6360322 | A | 3/1988 |
| JP | H01191674 | A | 8/1989 |
| JP | H0292986 | A | 4/1990 |
| JP | H0292988 | A | 4/1990 |
| JP | H02124081 | A | 5/1990 |
| JP | H02127493 | A | 5/1990 |
| JP | H02190171 | A | 7/1990 |
| JP | H0341185 | A | 2/1991 |
| JP | H03112478 | A | 5/1991 |
| JP | H03192677 | A | 8/1991 |
| JP | H03232481 | A | 10/1991 |
| JP | H05103836 | A | 4/1993 |
| JP | H05212100 | A | 8/1993 |
| JP | H05309136 | A | 11/1993 |
| JP | H062164 | B1 | 1/1994 |
| JP | H06189861 | A | 7/1994 |
| JP | H06315366 | A | 11/1994 |
| JP | H07147965 | A | 6/1995 |
| JP | H08942 | U | 6/1996 |
| JP | H08299862 | A | 11/1996 |
| JP | H08511175 | A | 11/1996 |
| JP | H08511176 | A | 11/1996 |
| JP | H09107943 | A | 4/1997 |
| JP | 3044574 | U | 12/1997 |
| JP | H1189551 | A | 4/1999 |
| JP | H11503912 | A | 4/1999 |
| JP | H11125390 | A | 5/1999 |
| JP | H11169157 | A | 6/1999 |
| JP | H11514081 | A | 11/1999 |
| JP | 2000119643 | A | 4/2000 |
| JP | 2001063776 | A | 3/2001 |
| JP | 2001509634 | A | 7/2001 |
| JP | 2002527153 | A | 8/2002 |
| JP | 2002529111 | A | 9/2002 |
| JP | 2004332069 | A | 11/2004 |
| JP | 2005036897 | A | 2/2005 |
| JP | 2005106350 | A | 4/2005 |
| JP | 2005524067 | A | 8/2005 |
| JP | 2005300005 | A | 10/2005 |
| JP | 2005537918 | A | 12/2005 |
| JP | 2005537919 | A | 12/2005 |
| JP | 2005538149 | A | 12/2005 |
| JP | 2005538159 | A | 12/2005 |
| JP | 2006501871 | A | 1/2006 |
| JP | 2006059640 | A | 3/2006 |
| JP | 2006219557 | A | 8/2006 |
| JP | 2007057532 | A | 3/2007 |
| JP | 2007512880 | A | 5/2007 |
| JP | 2008050422 | A | 3/2008 |
| JP | 2008511175 | A | 4/2008 |
| JP | 2008249003 | A | 10/2008 |
| JP | 2009509523 | A | 3/2009 |
| JP | 2009087703 | A | 4/2009 |
| JP | 2009537119 | A | 10/2009 |
| JP | 2009537120 | A | 10/2009 |
| JP | 2010506594 | A | 3/2010 |
| JP | 2010508034 | A | 3/2010 |
| JP | 2010178730 | A | 8/2010 |
| JP | 2010213579 | A | 9/2010 |
| JP | 2011058538 | A | 3/2011 |
| JP | 2011509667 | A | 3/2011 |
| JP | 2011515093 | A | 5/2011 |
| JP | 2011518567 | A | 6/2011 |
| JP | 2011525366 | A | 9/2011 |
| JP | 2012506263 | A | 3/2012 |
| JP | 2012529936 | A | 11/2012 |
| JP | 2012249854 | A | 12/2012 |
| JP | 2013507152 | A | 3/2013 |
| JP | 2013511962 | A | 4/2013 |
| JP | 5193668 | B2 | 5/2013 |
| JP | 2014511175 | A | 5/2014 |
| JP | 2014519586 | A | 8/2014 |
| JP | 2014521419 | A | 8/2014 |
| JP | 2015504653 | A | 2/2015 |
| JP | 2015513922 | A | 5/2015 |
| JP | 2015513970 | A | 5/2015 |
| JP | 2016521981 | A | 7/2016 |
| JP | 2016524777 | A | 8/2016 |
| JP | 2016526777 | A | 9/2016 |
| JP | 2016532432 | A | 10/2016 |
| JP | 2016538844 | A | 12/2016 |
| JP | 2017506915 | A | 3/2017 |
| JP | 6217980 | B2 | 10/2017 |
| JP | 6543357 | B2 | 7/2019 |
| KR | 950700692 | A | 2/1995 |
| KR | 19990081973 | A | 11/1999 |
| KR | 100385395 | B1 | 8/2003 |
| KR | 200350504 | Y1 | 5/2004 |
| KR | 200370872 | Y1 | 12/2004 |

(56)       References Cited

FOREIGN PATENT DOCUMENTS

| | | | |
|---|---|---|---|
| KR | 100636287 | B1 | 10/2006 |
| KR | 20070038350 | A | 4/2007 |
| KR | 100757450 | B1 | 9/2007 |
| KR | 20080060218 | A | 7/2008 |
| KR | 20100135865 | A | 12/2010 |
| KR | 20120012961 | A | 2/2012 |
| KR | 20120003484 | U | 5/2012 |
| KR | 20120104533 | A | 9/2012 |
| KR | 20120107914 | A | 10/2012 |
| KR | 20130006714 | A | 1/2013 |
| KR | 20130029697 | A | 3/2013 |
| KR | 20130038957 | A | 4/2013 |
| KR | 20130006714 | U | 11/2013 |
| KR | 20140063506 | A | 5/2014 |
| KR | 20150022407 | A | 3/2015 |
| KR | 20150047616 | A | 5/2015 |
| KR | 20160013208 | A | 2/2016 |
| KR | 20160097196 | A | 8/2016 |
| KR | 20160127793 | A | 11/2016 |
| MX | 2009001096 | A | 3/2009 |
| MX | 2014011283 | A | 10/2014 |
| RU | 2066337 | C1 | 9/1996 |
| RU | 2098446 | C1 | 12/1997 |
| RU | 2109468 | C1 | 4/1998 |
| RU | 2285028 | C1 | 10/2006 |
| RU | 2311859 | C2 | 12/2007 |
| RU | 2336001 | C2 | 10/2008 |
| RU | 2360583 | C1 | 7/2009 |
| RU | 89927 | U1 | 12/2009 |
| RU | 94815 | U1 | 6/2010 |
| RU | 103281 | U1 | 4/2011 |
| RU | 115629 | U1 | 5/2012 |
| RU | 2450780 | C2 | 5/2012 |
| RU | 122000 | U1 | 11/2012 |
| RU | 124120 | U1 | 1/2013 |
| RU | 2489948 | C2 | 8/2013 |
| RU | 132318 | U1 | 9/2013 |
| RU | 132954 | U1 | 10/2013 |
| RU | 2509516 | C2 | 3/2014 |
| WO | 8404698 | A1 | 12/1984 |
| WO | 8602528 | A1 | 5/1986 |
| WO | 9406314 | A1 | 3/1994 |
| WO | 9409842 | A1 | 5/1994 |
| WO | 9418860 | A1 | 9/1994 |
| WO | 9527411 | A1 | 10/1995 |
| WO | 9618662 | A1 | 6/1996 |
| WO | 9632854 | A2 | 10/1996 |
| WO | 9639879 | A1 | 12/1996 |
| WO | 9748293 | A1 | 12/1997 |
| WO | 9817131 | A1 | 4/1998 |
| WO | 9823171 | A1 | 6/1998 |
| WO | 9903308 | A1 | 1/1999 |
| WO | 9933008 | A2 | 7/1999 |
| WO | 0009188 | A1 | 2/2000 |
| WO | 0021598 | A1 | 4/2000 |
| WO | 0028842 | A1 | 5/2000 |
| WO | 0050111 | A1 | 8/2000 |
| WO | 0167819 | A1 | 9/2001 |
| WO | 02051468 | A2 | 7/2002 |
| WO | 02058747 | A1 | 8/2002 |
| WO | 02098389 | A1 | 12/2002 |
| WO | 03012565 | A1 | 2/2003 |
| WO | 03028409 | A1 | 4/2003 |
| WO | 03037412 | A2 | 5/2003 |
| WO | 03050405 | A1 | 6/2003 |
| WO | 03059413 | A2 | 7/2003 |
| WO | 03070031 | A1 | 8/2003 |
| WO | 03083283 | A1 | 10/2003 |
| WO | 03101454 | A1 | 12/2003 |
| WO | 03103387 | A2 | 12/2003 |
| WO | 2004022128 | A2 | 3/2004 |
| WO | 2004022242 | A1 | 3/2004 |
| WO | 2004022243 | A1 | 3/2004 |
| WO | 2004068901 | A2 | 8/2004 |
| WO | 2004089126 | A1 | 10/2004 |
| WO | 2005106350 | A2 | 11/2005 |
| WO | 2006082571 | A1 | 8/2006 |
| WO | 2007012007 | A2 | 1/2007 |
| WO | 2007017482 | A1 | 2/2007 |
| WO | 2007024130 | A1 | 3/2007 |
| WO | 2007040941 | A1 | 4/2007 |
| WO | 2007042941 | A2 | 4/2007 |
| WO | 2007051163 | A2 | 5/2007 |
| WO | 2007131449 | A1 | 11/2007 |
| WO | 2007131450 | A1 | 11/2007 |
| WO | 2007141668 | A2 | 12/2007 |
| WO | 2008038144 | A2 | 4/2008 |
| WO | 2008108889 | A1 | 9/2008 |
| WO | 2008113420 | A1 | 9/2008 |
| WO | 2008121610 | A1 | 10/2008 |
| WO | 2009001082 | A1 | 12/2008 |
| WO | 2009015410 | A1 | 2/2009 |
| WO | 2009022232 | A2 | 2/2009 |
| WO | 2009079641 | A2 | 6/2009 |
| WO | 2009092862 | A1 | 7/2009 |
| WO | 2009118085 | A1 | 10/2009 |
| WO | 2009132793 | A1 | 11/2009 |
| WO | 2010045670 | A1 | 4/2010 |
| WO | 2010045671 | A1 | 4/2010 |
| WO | 2010073018 | A1 | 7/2010 |
| WO | 2010102832 | A1 | 9/2010 |
| WO | 2010107613 | A1 | 9/2010 |
| WO | 2010118644 | A1 | 10/2010 |
| WO | 2010133342 | A1 | 11/2010 |
| WO | 2010145468 | A1 | 12/2010 |
| WO | 2011045609 | A1 | 4/2011 |
| WO | 2011050943 | A1 | 5/2011 |
| WO | 2011050964 | A1 | 5/2011 |
| WO | 2011063970 | A1 | 6/2011 |
| WO | 2011068020 | A1 | 6/2011 |
| WO | 2011079932 | A1 | 7/2011 |
| WO | 2011109849 | A1 | 9/2011 |
| WO | 2011130414 | A1 | 10/2011 |
| WO | 2012014490 | A1 | 2/2012 |
| WO | 2012025496 | A1 | 3/2012 |
| WO | 2012027350 | A2 | 3/2012 |
| WO | 2013022936 | A1 | 2/2013 |
| WO | 2013034453 | A1 | 3/2013 |
| WO | 2013034454 | A1 | 3/2013 |
| WO | 2013034458 | A1 | 3/2013 |
| WO | 2013034459 | A1 | 3/2013 |
| WO | 2013034460 | A1 | 3/2013 |
| WO | 2013057185 | A1 | 4/2013 |
| WO | 2013082173 | A1 | 6/2013 |
| WO | 2013083635 | A1 | 6/2013 |
| WO | 2013083638 | A1 | 6/2013 |
| WO | 2013098395 | A1 | 7/2013 |
| WO | 2013113612 | A1 | 8/2013 |
| WO | 2013116558 | A1 | 8/2013 |
| WO | 2013116572 | A1 | 8/2013 |
| WO | 2013131764 | A1 | 9/2013 |
| WO | 2013144324 | A1 | 10/2013 |
| WO | 2013152873 | A1 | 10/2013 |
| WO | 2013160112 | A2 | 10/2013 |
| WO | 2014012906 | A1 | 1/2014 |
| WO | 2014023964 | A1 | 2/2014 |
| WO | 2014023967 | A1 | 2/2014 |
| WO | 2014045025 | A2 | 3/2014 |
| WO | 2014048745 | A1 | 4/2014 |
| WO | 2014061477 | A1 | 4/2014 |
| WO | 2014078745 | A1 | 5/2014 |
| WO | 2014104078 | A1 | 7/2014 |
| WO | 2014130695 | A1 | 8/2014 |
| WO | 2014139609 | A2 | 9/2014 |
| WO | 2014139611 | A1 | 9/2014 |
| WO | 2014140320 | A1 | 9/2014 |
| WO | 2014150131 | A1 | 9/2014 |
| WO | 2014187763 | A1 | 11/2014 |
| WO | 2014194510 | A1 | 12/2014 |
| WO | 2014201432 | A1 | 12/2014 |
| WO | 2015000974 | A1 | 1/2015 |
| WO | 2015019099 | A1 | 2/2015 |
| WO | 2015019101 | A1 | 2/2015 |
| WO | 2015066127 | A1 | 5/2015 |

(56) References Cited

FOREIGN PATENT DOCUMENTS

| | | | | | |
|---|---|---|---|---|---|
| WO | 2015077645 | A1 | 5/2015 | | |
| WO | 2015082560 | A1 | 6/2015 | | |
| WO | 2015082648 | A1 | 6/2015 | | |
| WO | 2015082649 | A1 | 6/2015 | | |
| WO | 2015082651 | A1 | 6/2015 | | |
| WO | 2015082652 | A1 | 6/2015 | | |
| WO | 2015101479 | A1 | 7/2015 | | |
| WO | 2015114328 | A1 | 8/2015 | | |
| WO | 2015116934 | A1 | 8/2015 | | |
| WO | 2015117702 | A1 | 8/2015 | | |
| WO | 2015131058 | A1 | 9/2015 | | |
| WO | 2015150068 | A1 | 10/2015 | | |
| WO | 2015165812 | A1 | 11/2015 | | |
| WO | 2015175568 | A1 | 11/2015 | | |
| WO | 2015176898 | A1 | 11/2015 | | |
| WO | 2015177043 | A1 | 11/2015 | | |
| WO | 2015177044 | A1 | 11/2015 | | |
| WO | 2015177045 | A1 | 11/2015 | | |
| WO | 2015177046 | A1 | 11/2015 | | |
| WO | 2015177253 | A1 | 11/2015 | | |
| WO | 2015177254 | A1 | 11/2015 | | |
| WO | 2015177255 | A1 | 11/2015 | | |
| WO | 2015177256 | A1 | 11/2015 | | |
| WO | 2015177257 | A1 | 11/2015 | | |
| WO | 2015177264 | A1 | 11/2015 | | |
| WO | 2015177265 | A1 | 11/2015 | | |
| WO | WO-2015198015 | A1 | * 12/2015 | ............ | H05B 6/108 |
| WO | 2016075436 | A1 | 5/2016 | | |
| WO | 2016090952 | A1 | 6/2016 | | |
| WO | 2016162446 | A1 | 10/2016 | | |
| WO | 2017001819 | A1 | 1/2017 | | |
| WO | 2017005705 | A1 | 1/2017 | | |
| WO | 2017036950 | A2 | 3/2017 | | |
| WO | 2017036951 | A1 | 3/2017 | | |
| WO | 2017036954 | A1 | 3/2017 | | |
| WO | 2017036955 | A2 | 3/2017 | | |
| WO | 2017036957 | A1 | 3/2017 | | |
| WO | 2017036959 | A1 | 3/2017 | | |
| WO | 2017072147 | A2 | 5/2017 | | |
| WO | 2017072148 | A1 | 5/2017 | | |
| WO | 2017109448 | A2 | 6/2017 | | |
| WO | 2017072147 | A3 | 7/2017 | | |
| WO | 2017198837 | A1 | 11/2017 | | |
| WO | 2017198876 | A1 | 11/2017 | | |

OTHER PUBLICATIONS

Australian Examination Report, Application No. 2016313708, dated Nov. 23, 2018, 6 pages.

Brazilian Office Action for BR Application No. BR1120180085138, dated Dec. 11, 2019, 6 pages (2 pages of English Translation and 4 pages of Official Copy).

Brazilian Office Action, Application No. BR112017028541-0, dated Apr. 6, 2020, 4 pages.

Canadian Office Action for CA Application No. 3003521, dated Dec. 9, 2019, 6 pages.

Chinese First Office Action for Chinese Application No. 200980152395.4 date issued Dec. 3, 2012, 16 pages (10 pages of English Translation and 6 pages of Official Copy).

Chinese Office Action and Search Report, Application No. 201680038351.9, dated Sep. 16, 2019, 12 pages.

Chinese Office Action for CN Application No. 201680049091.5, dated Dec. 27, 2019, 25 pages (12 pages of English Translation and 13 pages of Official Copy).

Decision to Dismiss an Amendment received for Korean Patent Application No. 10-2017-7008071, mailed on Mar. 20, 2019, 3 pages (English Translation Only).

Decision to Grant a Patent received for Japanese Application No. 2015-506185 filed Apr. 11, 2013, mailed on Nov. 15, 2016, 5 pages (2 pages of English Translation and 3 pages of Official Copy).

Decision to Grant received for Japanese Patent Application No. 2011-532464, mailed on Aug. 5, 2014, 6 pages (3 pages of English Translation and 3 pages of Official Copy).

Decision to Grant received for Japanese Patent Application No. 2016-134648, mailed May 22, 2018, 5 pages (2 pages of English Translation and 3 pages of Official Copy).

Decision to Grant received for Russian Patent Application No. 2011120430, mailed on Apr. 1, 2014, 16 pages (6 pages of English Translation and 10 pages of Official Copy).

Decision to Grant received for Russian Patent Application No. 2014120213, mailed on Oct. 26, 2016, 7 pages (Official Copy Only).

European Notice of Opposition for JT International SA, Application No. EP 16731263.6, dated Mar. 11, 2020, 8 pages.

European Notice of Opposition for Philip Morris Products SA, Application No. EP 16731263.6, dated Mar. 11, 2020, 8 pages.

European Opposition Proceedings—Brief Communication, Application No. 16729350.5, dated Jul. 21, 2020, 17 pages.

European Search Report received for European Patent Application No. 16166656.5 dated Oct. 11, 2016, 9 pages (Official Copy Only).

Examination Report for Indian Application No. 201747046550, mailed on Jan. 9, 2020, 6 pages.

Examination Report received for Australian Patent Application No. 2016204192, mailed on Feb. 21, 2018, 7 pages.

Examination Report received for New Zealand Patent Application No. 718007, mailed on Aug. 1, 2016, 4 pages.

Examination Report received for Philippines Patent Application No. 1/2016/500805, mailed on Jan. 9, 2019, 6 pages.

Extended European Search Report for Application No. 18214130.9, mailed on May 10, 2019, 44 pages.

Extended European Search Report received for European Application No. 15178588.8, mailed on Apr. 22, 2016, 4 pages (Official Copy Only).

Extended European Search Report received for European Patent Application No. 15200661.5, mailed on May 18, 2016, 6 pages.

Extended European Search Report received for European Patent Application No. 18157257.9, mailed on Jun. 28, 2018, 7 pages.

Extended European Search Report received for European Patent Application No. 18205608.5, mailed on Jul. 12, 2019, 7 pages (Official Copy Only).

Extended European Search Report received for European Patent Application No. 17189951.1, mailed on Jan. 4, 2018, 11 pages (3 pages of English Translation and 8 pages of Official copy).

Final Office Action received for U.S. Appl. No. 15/739,024, filed Dec. 21, 2017, mailed on Apr. 10, 2020, 3 pages.

Final Office Action received for U.S. Appl. No. 15/739,037, filed Dec. 21, 2017, mailed on Sep. 25, 2019, 3 pages.

Final Office Action received for U.S. Appl. No. 15/739,024, filed Dec. 21, 2017, mailed on Oct. 3, 2019, 3 pages.

First Office Action filed Apr. 11, 2011, received for Chinese Application No. 201380021387.2, mailed on Dec. 3, 2015, 18 pages (12 pages of English Translation and 6 pages of Official Copy).

GB Search Report, Application No. GB1511359.0, dated Nov. 23, 2015, 3 pages.

Great Britain Search Report, Application No. GB1511349.1, dated Nov. 23, 2015, 5 pages.

Great Britain Search Report, Application No. GB1511361.6, dated Nov. 23, 2015, 5 pages.

India Examination Report, Application No. 201747046549, dated Feb. 14, 2020, 8 pages.

International Preliminary Report on Patentability for Application No. PCT/GB2015/051213 mailed on Jul. 14, 2016, 20 pages.

International Preliminary Report on Patentability for Application No. PCT/AT2012/000017, issued on Aug. 13, 2013, 5 pages.

International Preliminary Report on Patentability for Application No. PCT/EP2012/066484, mailed on Mar. 20, 2014, 7 pages.

International Preliminary Report on Patentability for Application No. PCT/EP2012/066485, completed on Dec. 20, 2013, 12 pages.

International Preliminary Report on Patentability for Application No. PCT/EP2012/066486, completed on Oct. 22, 2013, 10 pages.

International Preliminary Report on Patentability for Application No. PCT/EP2012/066523, completed on Nov. 4, 2013, 9 pages.

International Preliminary Report on Patentability for Application No. PCT/EP2012/066524, completed on Oct. 17, 2013, 11 pages.

International Preliminary Report on Patentability for Application No. PCT/EP2012/066525, completed on Mar. 20, 2014, 8 pages.

(56)         References Cited

OTHER PUBLICATIONS

International Preliminary Report on Patentability for Application No. PCT/EP2012/070647, mailed on May 1, 2014, 8 pages.
International Preliminary Report on Patentability for Application No. PCT/EP2014/063785, completed on Jun. 1, 2015, 12 pages.
International Preliminary Report on Patentability for Application No. PCT/EP2014/072828, mailed on May 12, 2016, 7 pages.
International Preliminary Report on Patentability for Application No. PCT/EP2015/064595, mailed on Oct. 25, 2016, 20 pages.
International Preliminary Report on Patentability for Application No. PCT/EP2016/075735, mailed on Jan. 2, 2018, 8 Pages.
International Preliminary Report on Patentability for Application No. PCT/EP2016/075737, mailed on May 11, 2018, 10 Pages.
International Preliminary Report on Patentability for Application No. PCT/EP2016/075738, mailed on May 11, 2018, 9 Pages.
International Preliminary Report on Patentability for Application No. PCT/GB2014/051332, mailed on Nov. 12, 2015, 7 pages.
"International Preliminary Report on Patentability for Application No. PCT/GB2014/051333, completed on Aug. 5, 2015", 12 pages.
International Preliminary Report on Patentability for Application No. PCT/GB2014/051334, mailed on Nov. 12, 2015, 7 pages.
International Preliminary Report on Patentability for Application No. PCT/GB2017/051139, completed on Aug. 6, 2018, 7 pages.
International Preliminary Report on Patentability for Application No. PCT/US2012/066523, mailed on Jun. 4, 2015, 6 pages.
International Preliminary Report on Patentability, Application No. PCT/GB2016/051730, mailed May 23, 2017, 14 pages.
International Preliminary Report on Patentability, Application No. PCT/GB2016/051767, mailed Apr. 18, 2018, 14 pages.
International Preliminary Report on Patentability, International Application No. PCT/GB2016/051731, mailed Jan. 11, 2018, 7 pages.
International Preliminary Report on Patentability, International Application No. PCT/GB2016/051766, dated Sep. 29, 2017, 11 pages.
International Search Report and Written Opinion for Application No. PCT/AT2011/000123, mailed on Jul. 18, 2011, 15 pages.
International Search Report and Written Opinion for Application No. PCT/EP2012/066484, mailed on Jan. 9, 2013, 9 pages.
International Search Report and Written Opinion for Application No. PCT/EP2012/066485, mailed on Dec. 10, 2012, 10 pages.
International Search Report and Written Opinion for Application No. PCT/EP2012/066486, mailed on Jan. 14, 2013, 8 pages.
International Search Report and Written Opinion for Application No. PCT/EP2012/066523, mailed on Jan. 9, 2013, 9 pages.
International Search Report and Written Opinion for Application No. PCT/EP2012/066524, mailed on Jan. 9, 2013, 8 pages.
International Search Report and Written Opinion for Application No. PCT/EP2012/066525, mailed on Jan. 9, 2013, 10 pages.
International Search Report and Written Opinion for Application No. PCT/EP2013/057539, mailed on Feb. 11, 2014, 16 Pages.
International Search Report and Written Opinion for Application No. PCT/EP2014/063785, mailed on Oct. 30, 2014, 10 pages.
International Search Report and Written Opinion for Application No. PCT/EP2014/064365, mailed on Oct. 7, 2014, 11 pages.
International Search Report and Written Opinion for Application No. PCT/EP2014/072828, mailed on Jun. 16, 2015, 10 pages.
International Search Report and Written Opinion for Application No. PCT/GB2016/051731, mailed on Sep. 20, 2016, 12 pages.
International Search Report and Written Opinion for Application No. PCT/GB2017/051139, mailed on Aug. 9, 2017, 14 pages.
International Search Report and Written Opinion received for PCT Application No. PCT/EP2012/003103, mailed on Nov. 26, 2012, 6 pages.
International Search Report and Written Opinion received for PCT Application No. PCT/GB2014/051333, mailed on Jul. 17, 2014, 10 pages.
International Search Report and Written Opinion received for PCT Application No. PCT/GB2014/051334 mailed Jul. 21, 2014, 8 pages.

International Search Report and Written Opinion received for PCT Application No. PCT/US2012/066523, mailed on May 29, 2013, 7 pages.
International Search Report and Written Opinion received for PCT Patent Application No. PCT/GB2014/051332, mailed on Jul. 21, 2014, 8 pages.
International Search Report and Written Opinion received for PCT Patent Application No. PCT/EP2012/070647, mailed on Feb. 6, 2013, 9 pages.
International Search Report and Written Opinion received for PCT Patent Application No. PCT/EP2016/070190, mailed Mar. 13, 2017, 19 pages.
International Search Report and Written Opinion received for PCT Patent Application No. PCT/EP2016/075736, mailed on Feb. 14, 2017, 8 pages.
International Search Report and Written Opinion received for PCT Patent Application No. PCT/AT2012/000017, mailed on Jul. 3, 2012, 13 pages (6 pages of English Translation and 7 pages of Official Copy).
International Search Report and Written Opinion received for PCT Patent Application No. PCT/EP2016/075737, mailed on Jun. 16, 2017, 17 pages.
International Search Report and Written Opinion, Application No. PCT/EP2016/075735, mailed Feb. 2, 2017, 9 pages.
International Search Report and Written Opinion, Application No. PCT/EP2016/075738, mailed Mar. 2, 2017, 13 pages.
International Search Report and Written Opinion, Application No. PCT/GB2016/051730, mailed Sep. 16, 2016, 13 pages.
International Search Report and Written Opinion, Application No. PCT/GB2016/051767, mailed Sep. 21, 2017, 23 pages.
International Search Report and Written Opinion, International Application No. PCT/GB2016/051766, mailed Sep. 27, 2016, 9 pages.
International Search Report for corresponding International Application No. PCT/GB2015/051213 mailed on Jul. 16, 2015, 5 pages.
International Search Report received for PCT Patent Application No. PCT/AT2009/000413 mailed on Jan. 25, 2010, 3 pages.
International Search Report received for PCT Patent Application No. PCT/AT2009/000414 mailed on Jan. 26, 2010, 2 pages.
International Search Report received for PCT Patent Application No. PCT/EP2015/064595, mailed on Jan. 5, 2016, 6 pages.
Japanese Decision to Grant, Application No. 2017-568122, dated Apr. 23, 2019, 5 pages.
Japanese Notice of Allowance, Application No. 2017-568256, dated Jun. 4, 2019, 5 pages.
Japanese Office Action for JP Application No. 2018-507621, dated Feb. 4, 2020, 29 pages (15 Pages of English Translation and 14 Pages of Official Copy).
Japanese Office Action, Application No. 2017-568122, dated Jan. 22, 2019, 5 pages.
Japanese Office Action, Application No. 2017-568123, dated Jan. 30, 2019, 3 pages (6 pages with translation).
Japanese Office Action, Application No. 2017-568124, dated Jan. 8, 2019, 8 pages.
Japanese Office Action, Application No. 2018-507621, dated May 7, 2019, 8 Pages (English Translation Only).
Japanese Office Action, Application No. 2018-519932, dated Jun. 25, 2019, 5 Pages (English Translation Only).
Japanese Office Action, Application No. 2018-521546, dated Jun. 25, 2019, 8 pages (4 pages of English Translation and 4 pages of Official Copy).
Japanese Office Action, Application No. 2018-521928, mailed Jul. 23, 2019, 14 pages (7 pages of English Translation and 7 pages of Official Copy).
Japanese Office Action, Application No. 2018-522061, dated Jul. 23, 2019, 9 pages (4 pages of English Translation and 5 pages of Official Copy).
Japanese Office Action, Application No. 2019-088015, dated Apr. 28, 2020, 20 pages.
Japanese Office Action, Application No. 2019-184922, dated Dec. 8, 2020, 8 pages (4 pages of English Translation and 4 pages of Official Copy).

(56) References Cited

OTHER PUBLICATIONS

"Kapton (Polyimide) Flexible Heaters", Kapton Flexible Heaters Guide, Available Online at <https://www.kapton-silicone-flexible-heaters.com/products/kapton_polyimide_flexible_heaters.html>, 2011, 2 pages.

Korean Notice of Allowance, Application No. 10-2017-7037789, dated Jun. 27, 2019, 4 pages.

Korean Office Action, Application No. 10-2017-7037789, mailed Dec. 25, 2018, 9 pages (18 pages with translation).

Korean Office Action, Application No. 10-2017-7037791, dated Dec. 25, 2018, 11 pages (22 pages with translation).

Korean Office Action, Application No. 10-2017-7037792, mailed Dec. 25, 2018, 11 pages (24 pages with translation).

Korean Office Action, Application No. 10-2017-7037793, dated Dec. 25, 2018, 11 pages (24 pages with translation).

Korean Office Action, Application No. 10-2018-7006076, dated Feb. 7, 2019, 10 Pages (English Translation Only).

Korean Office Action, Application No. 10-2018-7012353, dated Sep. 26, 2019, 14 pages (8 pages of English Translation and 6 pages of Official Copy).

Korean Office Action, Application No. 10-2018-7012366, dated Mar. 29, 2019, 12 pages (6 pages of English Translation and 6 pages of Official Copy).

Korean Office Action, Application No. 10-2018-7012422, dated Mar. 22, 2019, 19 pages (10 pages of Official Copy and 9 pages of English Translation).

Korean Office Action, Application No. 10-2018-7012428, dated Mar. 22, 2019, 15 pages (8 pages of English Translation and 7 pages of Official Copy).

Korean Office Action, Application No. 10-2019-7026377, dated Mar. 27, 2020, 16 pages.

Korean Office Action, Application No. 10-2019-7026720, dated Sep. 25, 2019, 17 pages.

"LDC Target Design", Texas Instruments, May 2017, 13 pages.

New Zealand First Examination Report, Application No. 738318, dated Sep. 19, 2018, 5 pages.

Notice of Allowance mailed Apr. 18, 2019 for Japanese Application No. 2017-568122, 2 pages.

Notice of Opposition Letter from EPO Opposition against for EP2358418 mailed on Mar. 1, 2017, 60 pages.

Notice of Opposition received for European Application No. 12750771.3, mailed on Jan. 11, 2019, 44 pages.

Notice of Opposition received for European Patent Application No. 12750765.5, mailed Sep. 26, 2018, 67 pages.

Notice of Opposition received for European Patent Application No. 12750770.5, mailed on Mar. 7, 2017, 22 pages.

Notice of Opposition received for European Patent Application No. 12750771.3, mailed on Jan. 24, 2019, 40 pages.

Notice of Opposition received for European Patent Application No. 12750771.3, mailed on Jan. 25, 2019, 2 pages.

Notice of Opposition, Application No. 16729350.5, dated Jan. 24, 2020, 77 pages.

Notice to File a Response received for Korean Application No. 10-2020-7019179, mailed on Mar. 22, 2022, 12 pages (7 pages of English Translation and 5 pages of Official Copy).

Notification of Reasons for Refusal received for Japanese Patent Application No. 2017-568123, mailed on Feb. 5, 2019, 6 pages.

Notification to Grant Patent Right received for Chinese Patent Application No. 201610086101.4, mailed on Oct. 25, 2018, 2 pages (English Translation Only).

Office Action and Search Report filed Aug. 24, 2012, for Chinese Patent Application No. 201280030681.5, mailed on Apr. 27, 2015, 25 pages (16 pages of English Translation and 9 pages of Official Copy).

Office Action and Search Report for Russian Application No. 2018141286, mailed on Feb. 3, 2022, 12 pages.

Office Action and Search Report mailed Sep. 29, 2019 for Chinese Application No. 201680038309.7, 25 pages.

Office Action and Search Report received for Chinese Patent Application No. 201680038254X, mailed on Sep. 30, 2019, 7 pages.

Office Action mailed Sep. 6, 2017 for Korean Application No. 10-2017-7017430, 9 pages.

Office Action mailed Jul. 21, 2020 for European Application No. 16729350.5 filed Apr. 17, 2019, 17 pages.

Office Action mailed Jul. 23, 2019 for Russian Application No. 2019100154, 11 pages.

Office Action received for Canadian Patent Application No. 2996341, mailed on Mar. 1, 2019, 4 pages.

Office Action received for Canadian Patent Application No. 3003520, mailed on Mar. 28, 2019, 3 pages.

Office Action received for Chinese Patent Application No. 201480024988.3, mailed on Dec. 30, 2016, 13 pages (English Translation Only).

Office Action received for Chinese Patent Application No. 201280029784.X, mailed on Jun. 15, 2015, 27 pages (16 pages of English Translation and 11 pages of Official Copy).

Office Action received for Chinese Patent Application No. 201380021387.2, mailed Jul. 8, 2016, 12 pages (7 pages of English Translation and 5 pages of Official Copy).

Office Action received for Chinese Patent Application No. 2013800472843, mailed on Nov. 13, 2017, 13 pages (7 pages of English Translation and 6 pages of Official Copy).

Office Action received for Chinese Patent Application No. 201480024978.X mailed on Jan. 18, 2017, 8 pages (5 pages of English Translation and 3 pages of Official Copy).

Office Action received for Chinese Patent Application No. 201480024988.3, mailed on Sep. 11, 2017, 10 pages (3 pages of English Translation and 7 pages of Official Copy).

Office Action received for Chinese Patent Application No. 201480037049.2, mailed on May 9, 2017, 28 pages (18 pages of English Translation and 10 pages of Official Copy).

Office Action received for Chinese Patent Application No. 201480059966.0, mailed on Dec. 26, 2017, 29 Pages (14 Pages of English Translation and 15 Pages of Official Copy).

Office Action received for Chinese Patent Application No. 201580022356.8, mailed on Jul. 18, 2018, 15 pages (7 pages of English Translation and 8 pages of Official Copy).

Office Action received for Chinese Patent Application No. 201580034981.4, mailed on Aug. 3, 2018, 17 pages (10 pages of English Translation and 7 pages of Official Copy).

Office Action received for Chinese Patent Application No. 201610086101.4, mailed on May 4, 2018, 7 pages (4 pages of English Translation and 3 pages of Official Copy).

Office Action received for Chinese Patent Application No. 201610371843.1, mailed on Sep. 30, 2018, 8 pages (5 pages of English Translation and 3 pages of Official Copy).

Office Action received for Chinese Patent Application No. 201610804046.8, mailed on Mar. 25, 2019, 17 pages (English Translation Only).

Office Action received for Chinese Patent Application No. 201710412726.X, mailed on Apr. 24, 2019, 21 pages (13 pages of English Translation and 8 pages of Official Copy).

Office Action received for Chinese Patent Application No. 201710413187.1, mailed on Apr. 24, 2019, 16 pages (9 pages of English Translation and 7 pages of Official Copy).

Office Action received for Chinese Patent Application No. 202010536674.9, mailed on Aug. 10, 2023, 21 pages (10 pages of English Translation and 11 pages of Official Copy).

Office Action received for Chinese Patent Application No. 2020105366749, mailed on Feb. 7, 2023, 13 pages (9 pages of English Translation and 4 pages of Official Copy Only).

Office Action received for Chinese Patent Application No. 202110460174.6, mailed on May 6, 2024, 9 pages (7 pages of English Translation and 2 pages of Official Copy).

Office Action received for European Patent Application No. 12750765.5, mailed on Sep. 25, 2018, 22 pages.

Office Action received for European Patent Application No. 17189951.1, mailed on Jan. 25, 2019, 4 pages (Official Copy Only).

Office Action received for Indian Patent Application No. 201647014549, mailed on Aug. 28, 2019, 6 pages.

Office Action received for Japanese Application No. 2015-506185, mailed on Sep. 29, 2015, 5 pages (2 pages of English Translation and 3 pages of Official Copy).

(56)  References Cited

OTHER PUBLICATIONS

Office Action received for Japanese Patent Application No. 2014-519585, mailed on Mar. 31, 2015, 8 pages (4 pages of English Translation and 4 pages of Official Copy).

Office Action received for Japanese Patent Application No. 2014-519586, mailed on Apr. 7, 2015, 10 pages (5 pages of English Translation and 5 pages of Official Copy).

Office Action received for Japanese Patent Application No. 2016-522550, mailed on Jan. 31, 2017, 7 Pages (3 Pages of English Translation and 4 Pages of Official Copy).

Office Action received for Japanese Patent Application No. 2016-522550, mailed on Jul. 4, 2017, 7 Pages (3 Pages of English Translation and 4 Pages of Official Copy).

Office Action received for Japanese Patent Application No. 2016-522550, mailed on Nov. 14, 2017, 6 pages (3 pages of English Translation and 3 pages of Official Copy).

Office Action received for Japanese Patent Application No. 2016-527295, mailed on Jun. 27, 2017, 8 pages (4 pages of English Translation and 4 pages of Official Copy).

Office Action received for Japanese Patent Application No. 2016-564977, mailed on Dec. 5, 2017, 6 pages (3 pages of English Translation and 3 pages of Official Copy).

Office Action received for Japanese Patent Application No. 2016-575543, mailed on Dec. 4, 2018, 19 pages (9 pages of English Translation and 10 pages of Official Copy).

Office Action received for Japanese Patent Application No. 2017-017842, mailed on Dec. 12, 2017, 6 pages (3 pages of English Translation and 3 pages of Official Copy).

Office Action received for Japanese Patent Application No. 2018-088088 mailed on Feb. 28, 2019, 25 pages (13 pages of English Translation and 12 pages of Official Copy).

Office Action received for Korean Patent Application No. 10-2013-7033866, mailed on Jul. 27, 2018, 22 pages (12 pages of English Translation and 10 pages of Official Copy).

Office Action received for Korean Patent Application No. 10-2014-7032958, mailed on Aug. 17, 2016, 13 pages (7 pages of English Translation and 6 pages of Official Copy).

Office Action received for Korean Patent Application No. 10-2016-7010831, mailed on Jul. 28, 2017, 11 pages (6 pages of English Translation and 5 pages of Official copy).

Office Action received for Korean Patent Application No. 10-2017-7008071, mailed on Mar. 20, 2019, 2 pages (English Translation Only).

Office Action received for Korean Patent Application No. 10-2017-7008071, mailed on May 11, 2018, 17 pages (9 pages of English Translation and 8 pages of Official Copy).

Office Action received for Korean Patent Application No. 10-2017-7017425, mailed on Sep. 6, 2017, 9 pages (5 pages of English Translation and 4 pages of Official Copy).

Office Action received for Korean Patent Application No. 10-2018-7017575, mailed on Jan. 23, 2019, 9 pages (5 pages of English Translation and 4 pages of Official Copy).

Office Action received for Korean Patent Application No. 10-2018-7019884, mailed on Apr. 5, 2019, 8 Pages (English Translation Only).

Office Action Received for Korean Patent Application No. 1020197037986, mailed on Feb. 6, 2020, 11 pages (5 pages of English Translation and 6 pages of Official copy).

Office Action received for Russian Patent Application No. 2015146847, mailed on Sep. 22, 2017, 11 pages (Official Copy Only).

Office Action received for Russian Patent Application No. 2016103729, mailed on Apr. 12, 2017, 10 pages (3 pages of English Translation and 7 pages of Official Copy).

Office Action received for Russian Patent Application No. 2018101312, mailed on Jul. 4, 2018, 11 pages (3 pages of English Translation and 8 pages of Official copy).

Office Action received for Russian Patent Application No. 2020112181, mailed on Jun. 9, 2023, 6 pages (Official Copy Only).

Reasons for Rejection received for Japanese Patent Application No. 2015-137361, mailed on May 31, 2016, 6 pages (3 pages of English Translation and 3 pages of Official Copy).

Reasons for Rejection received for Japanese Patent Application No. 2011-532464, mailed on Oct. 7, 2013, 6 pages (3 pages of English Translation and 3 pages of Official Copy).

Reasons for Rejection received for Japanese Patent Application No. 2014-179732, mailed on Sep. 8, 2015, 5 pages (2 pages of English Translation and 3 pages of Official Copy).

Reasons for Rejection received for Japanese Patent Application No. 2016-134648 mailed May 23, 2017, 18 pages (9 pages of English Translation and 9 pages of Official Copy).

Response to Second Written Opinion for Application No. PCT/GB2016/051767, filed Mar. 26, 2018, 12 pages.

Russian Decision to Grant, Application No. 2017145842, mailed Aug. 29, 2018, 12 pages.

Russian Decision to Grant, Application No. 2019102061, dated Jun. 19, 2019, 12 pages.

Russian Decision to Grant, Application No. 2019125736, dated Nov. 27, 2019, 12 pages.

Russian Office Action, Application No. 2018115542, dated Oct. 29, 2018, 9 pages (3 pages of English Translation and 6 pages of Official Copy).

Russian Office Action, Application No. 2019100154, dated Jun. 19, 2019, 6 pages.

Search Report mailed Nov. 23, 2015 for Great Britain Application No. 1511358.2, 3 pages.

Search Report received for Chinese Patent Application No. 201280029767.6, mailed on Mar. 24, 2015, 6 pages (3 pages of English Translation and 3 pages of Official Copy).

Search Report received for Chinese Patent Application No. 201610086101.4, mailed on Apr. 25, 2018, 1 page (English Translation Only).

Search Report received for Japanese Patent Application No. 2011-532464, mailed on Sep. 19, 2013, 116 pages (43 pages of English Translation and 73 pages of Official Copy).

Search Report received for Japanese Patent Application No. 2014-179732, mailed on Aug. 25, 2015, 10 pages (5 pages of English Translation and 5 pages of Official Copy).

Search Report received for Japanese Patent Application No. 2016-134648, mailed Mar. 28, 2017, 31 pages (20 pages of English Translation and 11 pages of Official Copy).

Search Report received for Japanese Patent Application No. 2016-564977, mailed on Oct. 25, 2017, 19 pages (10 pages of English Translation and 9 pages of Official Copy).

Search Report received for Russian Patent Application No. 2015146843/12 (072088), mailed on Apr. 24, 2017, 3 pages (English Translation Only).

Search Report received for Russian Patent Application No. 2018137501, mailed on Apr. 29, 2019, 12 pages (Official Copy Only).

Second Office Action received for Chinese Patent Application No. 200980152395.4, mailed on Aug. 20, 2013, 16 pages (10 pages of English Translation and 6 pages of Official Copy).

Second Office Action received for Chinese Patent Application No. 201380048636.7, mailed on Jan. 16, 2017, 23 pages (13 pages of English Translation and 10 pages of Official Copy).

Second Written Opinion, Application No. PCT/GB2016/051767, mailed Jan. 25, 2018, 5 pages.

Submission in Opposition proceedings for the European Application No. EP16729350.5, filed Jul. 20, 2020, 17 pages.

Substantive Examination Report mailed Oct. 25, 2019 for Malaysian Application No. PI2017704891, 2 pages.

Summons to Attend Oral Proceedings pursuant to Rule 115(1) EPC mailed Jan. 29, 2021 for European Application No. 16729350.5, 15 pages.

"Temperature-Sensitive Magnetic Alloys", NeoMax Materials Co. Ltd., Available Online at <http://www.neomax-materials.co.jp/eng/pr0510.htm>, Oct. 30, 2015, 2 pages.

"Welcome to Filtrona Porous Technologies", Filtrona Richmond Inc., Available Online at <http://www.filtronaporoustechnologies.com>, Nov. 19, 2018, 1 page.

Written Opinion for PCT Patent Application No. PCT/GB2015/051213 mailed on Jul. 16, 2015, 9 pages.

(56) References Cited

OTHER PUBLICATIONS

Written Opinion of the International Preliminary Examining Authority Received for PCT Application No. PCT/EP2015/064595, mailed on Jun. 13, 2016, 8 pages.

Written Opinion received for PCT Application No. PCT/EP2015/064595, mailed on Jan. 5, 2016, 11 pages.

Written Opinion received for PCT Patent Application No. PCT/EP2012/066485, mailed on Oct. 15, 2013, 6 pages.

Bstedh, "Induction Heating", Available at: https://www.e-cigaretteforum.com/forum/threas/induction-heatting.186526/, [Accessed Nov. 16, 2015], Apr. 5, 2011, 2 pages.

Collier et al., "Mechanism of Evaporation and Condensation", Convective Boiling and Condensation, Third Edition, Clarendon Press, 1994, 6 pages.

Concept Group, "Insulon® Thermal Barrier from Concept Group Blocks Heat with Hyper-Deep Vacuum™", Dec. 15, 2011, 1 page.

Concept Group, "New Super Insulator form Concept Group Stops Heat Conduction in Tight Spaces", https://www.businesswire.com/news/home/20110610006023/en/New-Super-Insulator-Concept-Group-Stops-Heat, 2011, 5 pages.

Davies et al., "Metallic Foams: Their Production, Properties and Applications", Journal of Materials Science, vol. 18, Part 7, 1983, pp. 1899-1911.

Diener Electronic, "Plasma Technology", The Company Diener Electronic GmbH+Co. KG, www.plasma.de, Oct. 17, 2017, 19 Pages.

Dunn et al., "Heat Pipes", 4th edition, ISBN 0080419038, 1994, 14 pages.

Evokevape, "Evoke—First Smart Vaporizer Powered by Induction", indiegogo.com, available at: https://www.indiegogo.com/projects/evoke-firstsmart-vaporizer-powered-by-induction#/, 2017, 5 pages.

Fraser, "Application and File History for U.S. Appl. No. 15/739,037, filed Dec. 21, 2017".

Fraser, "Application aacnd File History for U.S. Appl. No. 15/739,024, filed Dec. 21, 2017".

Fraser, "Application and File History for U.S. Appl. No. 15/739,029, filed Dec. 21, 2017".

Fraser, "Application and File History for U.S. Appl. No. 15/739,045, filed Dec. 21, 2017".

Grundas, "Advances in Induction and Microwave Heating of Mineral and Organic Materials", Ed. Intech., 2011, 226 pages.

Iorga et al., "Low Curie Temperature in Fe—Cr—Ni—Mn Alloys", U.P.B. Sci. Bull., Series B, vol. 73, Iss.4, 2011, pp. 195-202.

Kynol, "Standard Specifications of Kynol Activated Carbon Fiber Products", published by Kynol, Sep. 19, 2013, 2 pages.

Merriam-Webster, "Definition of Film", Available at <https://www.merriam-webster.com/dictionary/Film>, Sep. 17, 2019, 13 pages.

Patio Kits Direct, "Insulated Roof Panels", DIY Alumawood Patio Cover Kits, available at https://www.patiokitsdirect.com/about-insulation, Sep. 20, 2018, 2 pages.

Ramadan et al., "Customized Trapping of Magnetic Particles", 2009, 10 pages.

Rudolph, G, "The Influence of CO2 on the Sensory Characteristics of the Favor-System", BAT Cigarettenfabriken GmbH, http://legacy.library.ucsf.edu/tid/sla51f00, 1987, 24 pages.

Schmitt, "Electromagnetics Explained: A Handbook for V1fireless/RF, EMC, and High-Speed Electronics", Newnes, Elsevier Science, 2002, 55 pages.

Tipler et al., "Physics for Scientists and Engineers", 5th edition, W.H. Freeman and Company, 2004, pp. 860-863.

Todaka et al., "Low Curie Temperature Material for Induction Heating Self-Temperature Controlling System", Journal of Magnetism and Magnetic Materials 320, 2008, pp. e702-e707.

Warrier et al., "Effect of the Porous Structure of Graphite on Atomic Hydrogen Diffusion and Inventory", Nuclear Fusion, vol. 47, 2007, pp. 1656-1663.

Wikipedia, "Permeability (Electromagnetism)", Available at: https://en.wikipedia.org/wiki/Permeability (electromagnetism), Jan. 12, 2020, 10 pages.

Zinn et al., "Elements of Induction Heating: Design, Control and Applications", ASM International, Electric Power Research Institute, pp. 1, p. 245, 1988, 3 pages.

* cited by examiner

ELECTRONIC VAPOUR PROVISION SYSTEM

CROSS-REFERENCE TO RELATED APPLICATIONS

The present application is a continuation application of U.S. application Ser. No. 15/739,045, filed Dec. 21, 2017, which is a National Phase entry of PCT Application No. PCT/GB2016/051767, filed Jun. 15, 2016, which claims priority from GB Patent Application No. 1511361.6, filed Jun. 29, 2015, each of which is fully incorporated herein by reference.

FIELD

The present disclosure relates to electronic vapor provision systems such as electronic nicotine delivery systems (e.g. e-cigarettes).

BACKGROUND

FIG. 1 is a schematic diagram of one example of a conventional e-cigarette 10. The e-cigarette 10 has a generally cylindrical shape, extending along a longitudinal axis indicated by dashed line LA, and comprises two main components, namely a control unit 20 and a cartomizer 30. The cartomizer 30 includes an internal chamber containing a reservoir of liquid formulation including nicotine, a vaporizer (such as a heater), and a mouthpiece 35. The cartomizer 30 may further include a wick or similar facility to transport a small amount of liquid from the reservoir to the heater. The control unit 20 includes a re-chargeable battery to provide power to the e-cigarette 10 and a circuit board for generally controlling the e-cigarette 10. When the heater receives power from the battery, as controlled by the circuit board, the heater vaporizes the nicotine and this vapor (aerosol) is then inhaled by a user through the mouthpiece 35.

The control unit 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the control unit 20 and the cartomizer 30. The electrical connector on the control unit 20 that is used to connect to the cartomizer 30 also serves as a socket for connecting a charging device (not shown) when the control unit 20 is detached from the cartomizer 30. The cartomizer 30 may be detached from the control unit 20 and disposed of when the supply of nicotine is exhausted (and replaced with another cartomizer if so desired).

FIGS. 2 and 3 provide schematic diagrams of the control unit 20 and cartomizer 30, respectively, of the e-cigarette 10 of FIG. 1. Note that various components and details, e.g. such as wiring and more complex shaping, have been omitted from FIGS. 2 and 3 for reasons of clarity. As shown in FIG. 2, the control unit 20 includes a battery or cell 210 for powering the e-cigarette 10, as well as a chip, such as a (micro)controller for controlling the e-cigarette 10. The controller is attached to a small printed circuit board (PCB) 215 that also includes a sensor unit. If a user inhales on the mouthpiece 35, air is drawn into the e-cigarette 10 through one or more air inlet holes (not shown in FIGS. 1 and 2). The sensor unit detects this airflow, and in response to such a detection, the controller provides power from the battery 210 to the heater in the cartomizer 30.

As shown in FIG. 3, the cartomizer 30 includes an air passage 161 extending along the central (longitudinal) axis LA of the cartomizer 30 from the mouthpiece 35 to the connector 25A for joining the cartomizer 30 to the control unit 20. A reservoir 170 of nicotine-containing liquid is provided around the air passage 161. This reservoir 170 may be implemented, for example, by providing cotton or foam soaked in the liquid. The cartomizer 30 also includes a heater 155 in the form of a coil for heating liquid from reservoir 170 to generate vapor to flow through air passage 161 and out through mouthpiece 35. The heater 155 is powered through lines 166 and 167, which are in turn connected to opposing polarities (positive and negative, or vice versa) of the battery 210 via connector 25A.

One end of the control unit 20 provides a connector 25B for joining the control unit 20 to the connector 25A of the cartomizer 30. The connectors 25A and 25B provide mechanical and electrical connectivity between the control unit 20 and the cartomizer 30. The connector 25B includes two electrical terminals, an outer contact 240 and an inner contact 250, which are separated by insulator 260. The connector 25A likewise includes an inner electrode 175 and an outer electrode 171, separated by insulator 172. When the cartomizer 30 is connected to the control unit 20, the inner electrode 175 and the outer electrode 171 of the cartomizer 30 engage the inner contact 250 and the outer contact 240, respectively, of the control unit 20. The inner contact 250 is mounted on a coil spring 255 so that the inner electrode 175 pushes against the inner contact 250 to compress the coil spring 255, thereby helping to ensure good electrical contact when the cartomizer 30 is connected to the control unit 20.

The cartomizer connector 25A is provided with two lugs or tabs 180A, 180B, which extend in opposite directions away from the longitudinal axis LA of the e-cigarette 10. These tabs 180A, 180B are used to provide a bayonet fitting for connecting the cartomizer 30 to the control unit 20. It will be appreciated that other embodiments may use a different form of connection between the control unit 20 and the cartomizer 30, such as a snap fit or a screw connection.

As mentioned above, the cartomizer 30 is generally disposed of once the liquid reservoir 170 has been depleted, and a new cartomizer 30 is purchased and installed. In contrast, the control unit 20 is re-usable with a succession of cartomizers 30. Accordingly, it is particularly desirable to keep the cost of the cartomizer 30 relatively low. One approach to doing this has been to construct a three-part device, based on (i) a control unit, (ii) a vaporizer component, and (iii) a liquid reservoir. In this three-part device, only the final part, the liquid reservoir, is disposable, whereas the control unit and the vaporizer are both re-usable. However, having a three-part device can increase the complexity, both in terms of manufacture and user operation. Moreover, it can be difficult in such a 3-part device to provide a wicking arrangement of the type shown in FIG. 3 to transport liquid from the reservoir to the heater.

Another approach is to make the cartomizer 30 re-fillable, so that it is no longer disposable. However, making a cartomizer re-fillable brings potential problems, for example, a user may try to re-fill the cartomizer with an inappropriate liquid (one not provided by the supplier of the e-cigarette). There is a risk that this inappropriate liquid may result in a low quality consumer experience, and/or may be potentially hazardous, whether by causing damage to the e-cigarette itself, or possibly by creating toxic vapors.

Accordingly, existing approaches for reducing the cost of a disposable component (or for avoiding the need for such a disposable component) have met with only limited success.

SUMMARY

The invention is defined in the appended claims.

Various embodiments of the disclosure provide an electronic vapor provision system having a longitudinal axis. The electronic vapor provision system comprises a control unit and at least one cartridge configured to engage with and disengage from the control unit substantially along said longitudinal axis. The at least one cartridge includes a reservoir of liquid to be vaporized. The electronic vapor provision system further comprises an induction heating assembly comprising at least one drive coil and a plurality of heater elements. The heaters elements are located in the at least one cartridge for vaporizing said liquid. The at least one cartridge is configured to feed liquid from the reservoir onto the heater elements for vaporization. The at least one cartridge is located, when engaged with the control unit, such that the heater elements are within the at least one drive coil. The electronic vapor provision system is configured to support selective energization of different heater elements from the plurality of heater elements.

The approach described herein is not restricted to specific embodiments such as set out below, but includes and contemplates any appropriate combinations of features presented herein. For example, an electronic vapor provision system may be provided in accordance with the approach described herein which includes any one or more of the various features described below as appropriate.

BRIEF DESCRIPTION OF THE DRAWINGS

Various embodiments of the disclosure will now be described in detail by way of example only with reference to the following drawings.

DETAILED DESCRIPTION

Figure 4:
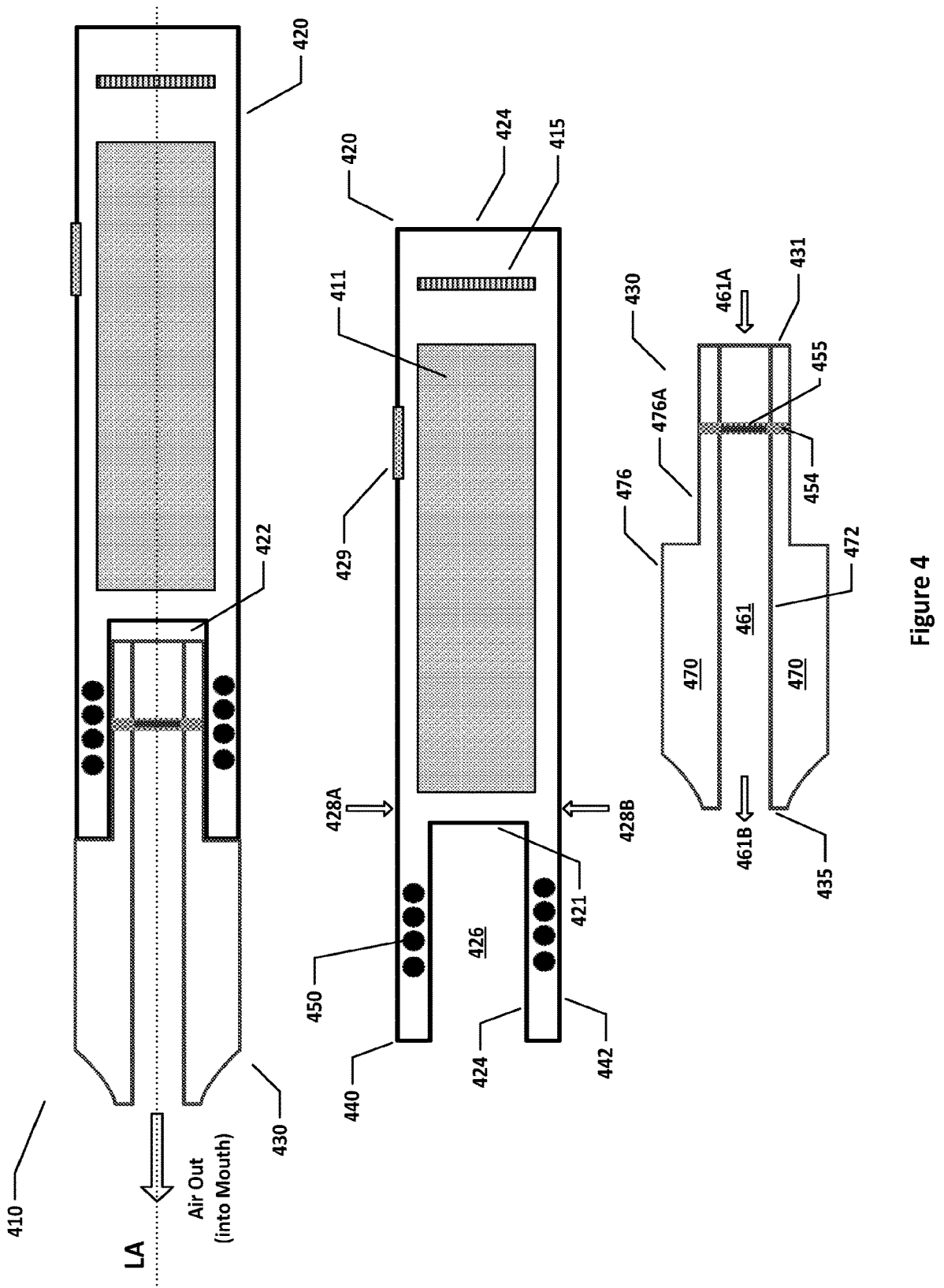
FIG. 4 is a schematic diagram illustrating an e-cigarette in accordance with some embodiments of the disclosure, showing the control unit assembled with the cartridge (top), the control unit by itself (middle), and the cartridge by itself (bottom).

FIG. 4 is a schematic diagram illustrating an e-cigarette 410 in accordance with some embodiments of the disclosure (please note that the term e-cigarette is used herein interchangeably with other similar terms, such as electronic vapor provision system, electronic aerosol provision system, etc.). The e-cigarette 410 includes a control unit 420 and a cartridge 430. FIG. 4 shows the control unit 420 assembled with the cartridge 430 (top), the control unit 420 by itself (middle), and the cartridge 430 by itself (bottom). Note that for clarity, various implementation details (e.g. such as internal wiring, etc.) are omitted.

Figures 1, 2:
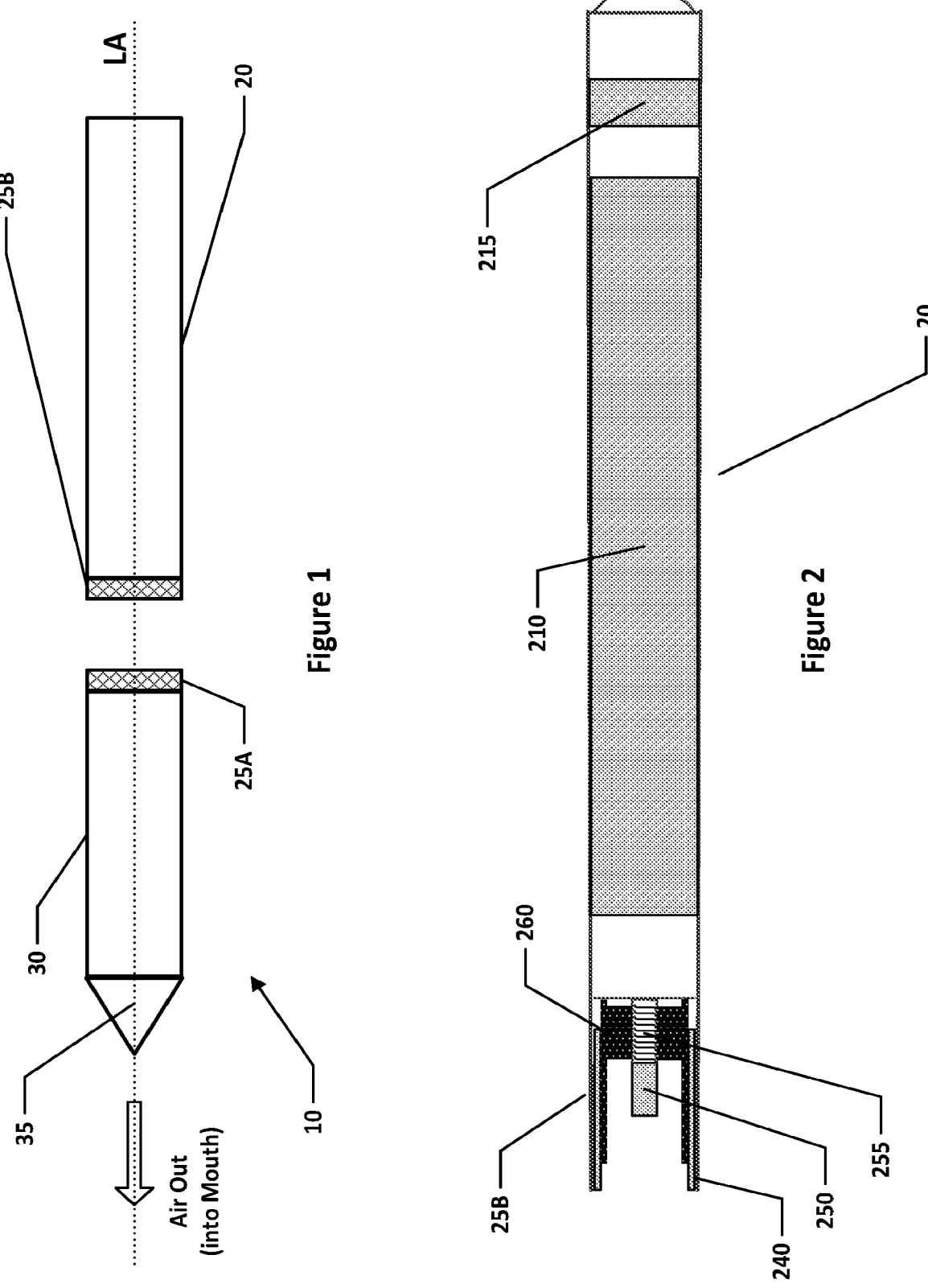
FIG. 1 is a schematic (exploded) diagram illustrating an example of a known e-cigarette.
FIG. 2 is a schematic diagram of the control unit of the e-cigarette of FIG. 1.
Figure 3:
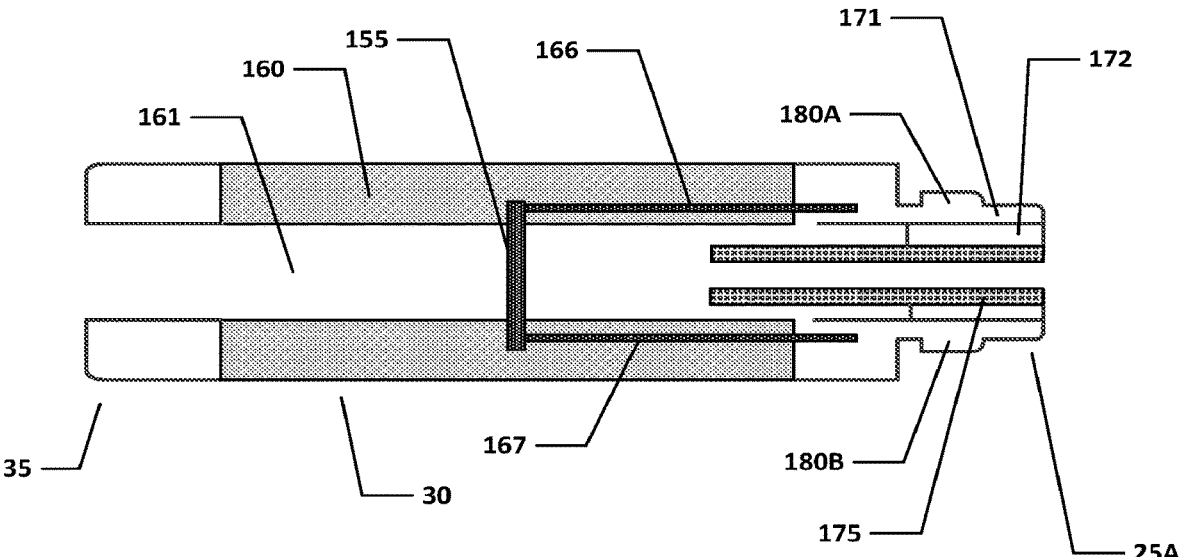
FIG. 3 is a schematic diagram of the cartomizer of the e-cigarette of FIG. 1.

As shown in FIG. 4, the e-cigarette 410 has a generally cylindrical shape with a central, longitudinal axis (denoted as LA, shown in dashed line). Note that the cross-section through the cylinder, i.e. in a plane perpendicular to the line LA, may be circular, elliptical, square, rectangular, hexagonal, or some other regular or irregular shape as desired. The general profile and shape (form factor) of the e-cigarette 410 is (or can be arranged to be) the same or broadly similar to that of e-cigarette 10 as shown in FIGS. 1-3. This consistency can be helpful for various reasons, such as potential to share components and packaging, user acceptance and ease of operation, brand recognition, etc.

The mouthpiece 435 is located at one end of the cartridge 430, while the opposite end of the e-cigarette 410 (with respect to the longitudinal axis LA) is denoted as the tip end 424. The end of the cartridge 430 which is longitudinally opposite to the mouthpiece 435 is denoted by reference numeral 431, while the end of the control unit 420 which is longitudinally opposite to the tip end 424 is denoted by reference numeral 421.

The cartridge 430 is able to engage with and disengage from the control unit 420 by movement along the longitudinal axis LA. More particularly, the end 431 of the cartridge is able to engage with, and disengage from, the end of the control unit 421. Accordingly, ends 421 and 431 will be referred to as the control unit engagement end and the cartridge engagement end, respectively.

The control unit 420 includes a battery 411 and a circuit board 415 to provide control functionality for the e-cigarette 410, e.g. by provision of a controller, processor, ASIC or similar form of control chip. The battery 411 is typically cylindrical in shape, and has a central axis that lies along, or at least close to, the longitudinal axis LA of the e-cigarette 410. In FIG. 4, the circuit board 415 is shown longitudinally spaced from the battery 411, in the opposite direction to the cartridge 430. However, the skilled person will be aware of various other locations for the circuit board 415, for example, it may be at the opposite end of the battery 411. A further possibility is that the circuit board 415 lies along the side of the battery 411—for example, with the e-cigarette 410 having a rectangular cross-section, the circuit board 415 located adjacent one outer wall of the e-cigarette 410, and the battery 411 then slightly offset towards the opposite outer wall of the e-cigarette 410. Note also that the functionality provided by the circuit board 415 (as described in more detail below) may be split across multiple circuit boards and/or across devices which are not mounted to a PCB, and these additional devices and/or PCBs can be located as appropriate within the e-cigarette 410.

The battery or cell 411 is generally re-chargeable, and one or more re-charging mechanisms may be supported. For example, a charging connection (not shown in FIG. 4) may be provided at the tip end 424, and/or the engagement end 421, and/or along the side of the e-cigarette 410. Moreover, the e-cigarette 410 may support induction re-charging of battery 411, in addition to (or instead of) re-charging via one or more re-charging connections or sockets.

The control unit 420 includes a tube portion 440, which extends along the longitudinal axis LA away from the engagement end 421 of the control unit 420. The tube portion 440 is defined on the outside by outer wall 442, which may generally be part of the overall outer wall or housing of the control unit 420, and on the inside by inner wall 424. A cavity 426 is formed by inner wall 424 of the tube portion and the engagement end 421 of the control unit 420. This cavity 426 is able to receive and accommodate at least part of a cartridge 430 as it engages with the control unit 420 (as shown in the top drawing of FIG. 4).

The inner wall 424 and the outer wall 442 of the tube portion 440 define an annular space which is formed around the longitudinal axis LA. A (drive or work) coil 450 is located within this annular space, with the central axis of the coil 450 being substantially aligned with the longitudinal axis LA of the e-cigarette 410. The coil 450 is electrically connected to the battery 411 and circuit board 415, which provide power and control to the coil 450, so that in operation, the coil 450 is able to provide induction heating to the cartridge 430.

The cartridge 430 includes a reservoir 470 containing liquid formulation (typically including nicotine). The reservoir 470 comprises a substantially annular region of the cartridge 430, formed between an outer wall 476 of the cartridge 430, and an inner tube or wall 472 of the cartridge 430, both of which are substantially aligned with the longitudinal axis LA of the e-cigarette 410. The liquid formulation may be held free within the reservoir 470, or alternatively the reservoir 470 may incorporated in some structure or material, e.g. sponge, to help retain the liquid within the reservoir 470.

The outer wall 476 has a portion 476A of reduced cross-section. This allows this portion 476A of the cartridge 430 to be received into the cavity 426 in the control unit 420 in order to engage the cartridge 430 with the control unit 420. The remainder of the outer wall 476 has a greater cross-section in order to provide increased space within the reservoir 470, and also to provide a continuous outer surface for the e-cigarette 410—i.e. cartridge wall 476 is substantially flush with the outer wall 442 of the tube portion 440 of the control unit 420. However, it will be appreciated that other implementations of the e-cigarette 410 may have a more complex/structured outer surface (compared with the smooth outer surface shown in FIG. 4).

The inside of the inner tube 472 defines a passageway 461 which extends, in a direction of airflow, from air inlet 461A (located at the end 431 of the cartridge 430 that engages the control unit 420) through to air outlet 461B, which is provided by the mouthpiece 435. Located within the central passageway 461, and hence within the airflow through the cartridge, are heater 455 and wick 454. As can be seen in FIG. 4, the heater 455 is located approximately in the center of the drive coil 450. In particular, the location of the heater 455 along the longitudinal axis LA can be controlled by having the step at the start of the portion 476A of reduced cross-section for the cartridge 430 abut against the end (nearest the mouthpiece 435) of the tube portion 440 of the control unit 420 (as shown in the top diagram of FIG. 4).

The heater 455 is made of a metallic material so as to permit use as a susceptor (or workpiece) in an induction heating assembly. More particularly, the induction heating assembly comprises the drive (work) coil 450, which produces a magnetic field having high frequency variations (when suitably powered and controlled by the battery 411 and controller on PCB 415). This magnetic field is strongest in the center of the coil, i.e. within cavity 426, where the heater 455 is located. The changing magnetic field induces eddy currents in the conductive heater 455, thereby causing resistive heating within the heater element 455. Note that the high frequency of the variations in magnetic field causes the eddy currents to be confined to the surface of the heater element 455 (via the skin effect), thereby increasing the effective resistance of the heating element 455, and hence the resulting heating effect.

Furthermore, the heater element 455 is generally selected to be a magnetic material having a high permeability, such as (ferrous) steel (rather than just a conductive material). In this case, the resistive losses due to eddy currents are supplemented by magnetic hysteresis losses (caused by repeated flipping of magnetic domains) to provide more efficient transfer of power from the drive coil 450 to the heater element 455.

The heater 455 is at least partly surrounded by wick 454. Wick 454 serves to transport liquid from the reservoir 470 onto the heater 455 for vaporization. The wick 454 may be made of any suitable material, for example, a heat-resistant, fibrous material and typically extends from the passageway 461 through holes in the inner tube 472 to gain access into the reservoir 470. The wick 454 is arranged to supply liquid to the heater 455 in a controlled manner, in that the wick 454 prevents the liquid leaking freely from the reservoir 470 into passageway 461 (this liquid retention may also be assisted by having a suitable material within the reservoir itself). Instead, the wick 454 retains the liquid within the reservoir 470, and on the wick 454 itself, until the heater 455 is activated, whereupon the liquid held by the wick 454 is vaporized into the airflow, and hence travels along passageway 461 for exit via mouthpiece 435. The wick 454 then draws further liquid into itself from the reservoir 470, and the process repeats with subsequent vaporizations (and inhalations) until the cartridge 430 is depleted.

Although the wick 454 is shown in FIG. 4 as separate from (albeit encompassing) the heater element 455, in some implementations, the heater element 455 and wick 454 may be combined together into a single component, such as a heating element 455 made of a porous, fibrous steel material which can also act as a wick 454 (as well as a heater). In addition, although the wick 454 is shown in FIG. 4 as supporting the heater element 455, in other embodiments, the heater element 455 may be provided with separate supports, for example, by being mounted to the inside of tube 472 (instead of or in addition to being supported by the heater element 455).

The heater 455 may be substantially planar, and perpendicular to the central axis of the coil 450 and the longitudinal axis LA of the e-cigarette 410, since induction primarily occurs in this plane. Although FIG. 4 shows the heater 455 and wick 454 extending across the full diameter of the inner tube 472, typically the heater 455 and wick 454 will not cover the whole cross-section of the air passage-way 461. Instead, space is typically provided to allow air to flow through the inner tube from inlet 461A and around heater 455 and wick 454 to pick up the vapor produced by the heater 455. For example, when viewed along the longitudinal axis LA, the heater 455 and wick 454 may have an "O" configuration with a central hole (not shown in FIG. 4) to allow for airflow along the passageway 461. Many other configurations are possible, such as the heater 455 having a "Y" or "X" configuration. (Note that in such implementations, the arms of the "Y" or X" would be relatively broad to provide better induction.)

Although FIG. 4 shows the engagement end 431 of the cartridge 430 as covering the air inlet 461A, this end of cartridge 430 may be provided with one or more holes (not shown in FIG. 4) to allow the desired air intake to be drawn into passageway 461. Note also that in the configuration shown in FIG. 4, there is a slight gap 422 between the engagement end 431 of the cartridge 430 and the corresponding engagement end 421 of the control unit 420. Air can be drawn from this gap 422 through air inlet 461A.

The e-cigarette 410 may provide one or more routes to allow air to initially enter the gap 422. For example, there may be sufficient spacing between the outer wall 476A of the cartridge 430 and the inner wall 444 of tube portion 440 to allow air to travel into gap 422. Such spacing may arise naturally if the cartridge 430 is not a tight fit into the cavity 426. Alternatively one or more air channels may be provided as slight grooves along one or both of these walls 476A, 444 to support this airflow. Another possibility is for the housing of the control unit 420 to be provided with one or more holes, firstly to allow air to be drawn into the control unit 420, and then to pass from the control unit into gap 422. For example, the holes for air intake into the control unit 420 might be positioned as indicated in FIG. 4 by arrows 428A and 428B, and engagement end 421 might be provided with one or more holes (not shown in FIG. 4) for the air to pass out from the control unit 420 into gap 422 (and from there into the cartridge 430). In other implementations, gap 422 may be omitted, and the airflow may, for example, pass directly from the control unit 420 through the air inlet 461A into the cartridge 430.

The e-cigarette 410 may be provided with one or more activation mechanisms for the induction heater assembly, i.e. to trigger operation of the drive coil 450 to heat the heating element 455. One possible activation mechanism is to provide a button 429 on the control unit 420, which a user may press to active the heater 455. This button may be a mechanical device, a touch sensitive pad, a sliding control, etc. The heater 455 may stay activated for as long as the user continues to press or otherwise positively actuate the button 429, subject to a maximum activation time appropriate to a single puff of the e-cigarette 410 (typically a few seconds). If this maximum activation time is reached, the controller may automatically de-activate the induction heater to prevent over-heating. The controller may also enforce a minimum interval (again, typically for a few seconds) between successive activations.

The induction heater assembly may also be activated by airflow caused by a user inhalation. In particular, the control unit 420 may be provided with an airflow sensor for detecting an airflow (or pressure drop) caused by an inhalation. The airflow sensor is then able to notify the controller of this detection, and the induction heater is activated accordingly. The induction heater may remain activated for as long as the airflow continues to be detected, subject again to a maximum activation time as above (and typically also a minimum interval between puffs).

Airflow actuation of the heater may be used instead of providing button 429 (which could therefore be omitted), or alternatively the e-cigarette 410 may require dual activation in order to operate—i.e. both the detection of airflow and the pressing of button 429. This requirement for dual activation can help to provide a safeguard against unintended activation of the e-cigarette 410.

It will be appreciated that the use of an airflow sensor generally involves an airflow passing through the control unit 420 upon inhalation, which is amenable to detection (even if this airflow only provides part of the airflow that the user ultimately inhales). If no such airflow passes through the control unit 420 upon inhalation, then button 429 may be used for activation, although it might also be possible to provide an airflow sensor to detect airflow passing across a surface of (rather than through) the control unit 420.

There are various ways in which the cartridge 430 may be retained within the control unit 420. For example, the inner wall 444 of the tube portion 440 of the control unit 420 and the outer wall of reduced cross-section 476A may each be provided with a screw thread (not shown in FIG. 4) for mutual engagement. Other forms of mechanical engagement, such as a snap fit, a latching mechanism (perhaps with a release button or similar) may also be used. Furthermore, the control unit 420 may be provided with additional components to provide a fastening mechanism, such as described below.

In general terms, the attachment of the cartridge 430 to the control unit 420 for the e-cigarette 410 of FIG. 4 is simpler than in the case of the e-cigarette 10 shown in FIGS. 1-3. In particular, the use of induction heating for e-cigarette 410 allows the connection between the cartridge 430 and the control unit 420 to be mechanical only, rather than also having to provide an electrical connection with wiring to a resistive heater. Consequently, the mechanical connection may be implemented, if so desired, by using an appropriate plastic molding for the housing of the cartridge 430 and the control unit 420; in contrast, in the e-cigarette 10 of FIGS. 1-3, the housings of the cartomizer 30 and the control unit 20 have to be somehow bonded to a metal connector. Furthermore, the connector of the e-cigarette 10 of FIGS. 1-3 has to be made in a relatively precise manner to ensure a reliable, low contact resistance, electrical connection between the control unit 20 and the cartomizer 30. In contrast, the manufacturing tolerances for the purely mechanical connection between the cartridge 430 and the control unit 420 of e-cigarette 410 are generally greater. These factors all help to simplify the production of the cartridge 430 and thereby to reduce the cost of this disposable (consumable) component.

Furthermore, conventional resistive heating often utilizes a metallic heating coil surrounding a fibrous wick, however, it is relatively difficult to automate the manufacture of such a structure. In contrast, an inductive heating element 455 is typically based on some form of metallic disk (or other substantially planar component), which is an easier structure to integrate into an automated manufacturing process. This again helps to reduce the cost of production for the disposable cartridge 430.

Another benefit of inductive heating is that conventional e-cigarettes may use solder to bond power supply wires to a resistive heater coil. However, there is some concern that heat from the coil during operation of such an e-cigarette might volatize undesirable components from the solder, which would then be inhaled by a user. In contrast, there are no wires to bond to the inductive heater element 455, and hence the use of solder can be avoided within the cartridge 430. Also, a resistive heater coil as in a conventional e-cigarette generally comprises a wire of relatively small diameter (to increase the resistance and hence the heating effect). However, such a thin wire is relatively delicate and so may be susceptible to damage, whether through some mechanical mistreatment and/or potentially by local over-heating and then melting. In contrast, a disk-shaped heater element 455 as used for induction heating is generally more robust against such damage.

Figures 5, 6:
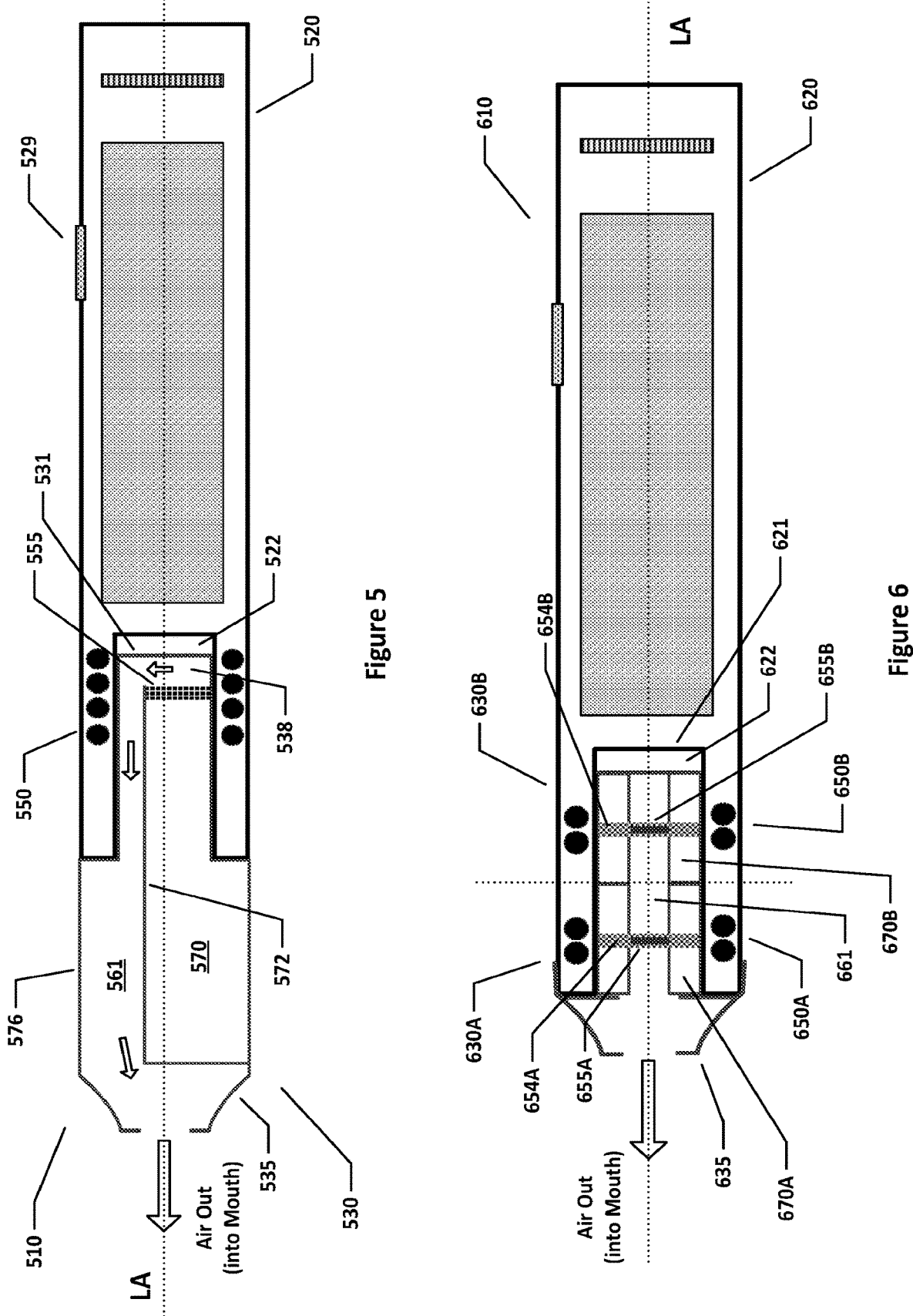
FIGS. 5 and 6 are schematic diagrams illustrating an e-cigarette in accordance with some other embodiments of the disclosure.

FIGS. 5 and 6 are schematic diagrams illustrating an e-cigarette 510, 610 in accordance with some other embodiments of the invention. To avoid repetition, aspects of FIGS. 5 and 6 that are generally the same as shown in FIG. 4 will not be described again, except where relevant to explain the particular features of FIGS. 5 and 6. Note also that reference numbers having the same last two digits typically denote the same or similar (or otherwise corresponding) components across FIGS. 4 to 6 (with the first digit in the reference number corresponding to the Figure containing that reference number).

In the e-cigarette shown in FIG. 5, the control unit 520 is broadly similar to the control unit 420 shown in FIG. 4, however, the internal structure of the cartridge 530 is somewhat different from the internal structure of the cartridge 430 shown in FIG. 4. Thus rather than having a central airflow passage, as for e-cigarette 410 of FIG. 4, in which the liquid reservoir 470 surrounds the central airflow passage 461, in the e-cigarette 510 of FIG. 5, the air passageway 561 is offset from the central, longitudinal axis (LA) of the cartridge 530. In particular, the cartridge 530 contains an internal wall 572 that separates the internal space of the cartridge 530 into two portions. A first portion, defined by internal wall 572 and one part of external wall 576, provides a chamber for holding the reservoir 570 of liquid formulation. A second portion, defined by internal wall 572 and an opposing part of external wall 576, defines the air passageway 561 through the e-cigarette 510.

In addition, the e-cigarette 510 does not have a wick, but rather relies upon a porous heater element 555 to act both as the heating element (susceptor) and the wick to control the flow of liquid out of the reservoir 570. The porous heater element 555 may be made, for example, of a material formed from sintering or otherwise bonding together steel fibers.

The heater element 555 is located at the end of the reservoir 570 opposite to the mouthpiece 535 of the cartridge 530, and may form some or all of the wall of the reservoir chamber 570 at this end. One face of the heater element 555 is in contact with the liquid in the reservoir 570, while the opposite face of the heater element 555 is exposed to an airflow region 538 which can be considered as part of air passageway 561. In particular, this airflow region 538 is located between the heater element 555 and the engagement end 531 of the cartridge 530.

When a user inhales on mouthpiece 435, air is drawn into the region 538 through the engagement end 531 of the cartridge 530 from gap 522 (in a similar manner to that described for the e-cigarette 410 of FIG. 4). In response to the airflow (and/or in response to the user pressing button 529), the coil 550 is activated to supply power to heater 555, which therefore produces a vapor from the liquid in reservoir 570. This vapor is then drawn into the airflow caused by the inhalation, and travels along the passageway 561 (as indicated by the arrows) and out through mouthpiece 535.

In the e-cigarette 610 shown in FIG. 6, the control unit 620 is broadly similar to the control unit 420 shown in FIG. 4, but now accommodates two (smaller) cartridges 630A, and 630B. Each of these cartridges 630A, 630B is analogous in structure to the reduced cross-section portion 476A of the cartridge 420 in FIG. 4. However, the longitudinal extent of each of the cartridges 630A and 630B is only half that of the reduced cross-section portion 476A of the cartridge 420 in FIG. 4, thereby allowing two cartridges 630A, 630B to be contained within the region in e-cigarette 610 corresponding to cavity 426 in e-cigarette 410, as shown in FIG. 4. In addition, the engagement end 621 of the control unit 620 may be provided, for example, with one or more struts or tabs (not shown in FIG. 6) that maintain cartridges 630A, 630B in the position shown in FIG. 6 (rather than closing the gap region 622).

In the e-cigarette 610, the mouthpiece 635 may be regarded as part of the control unit 620. In particular, the mouthpiece 635 may be provided as a removable cap or lid, which can screw or clip onto and off the remainder of the control unit 620 (or any other appropriate fastening mechanism can be used). The mouthpiece cap 635 is removed from the rest of the control unit 635 to insert a new cartridge or to remove an old cartridge, and then fixed back onto the control unit for use of the e-cigarette 610.

The operation of the individual cartridges 630A, 630B in e-cigarette 610 is similar to the operation of cartridge 430 in e-cigarette 410, in that each cartridge includes a wick 654A, 654B extending into the respective reservoir 670A, 670B. In addition, each cartridge 630A, 630B includes a heating element, 655A, 655B, accommodated in a respective wick, 654A, 654B, and may be energized by a respective coil 650A, 650B provided in the control unit 620. The heaters 655A, 655B vaporize liquid into a common passageway 661 that passes through both cartridges 630A, 630B and out through mouthpiece 635.

The different cartridges 630A, 630B may be used, for example, to provide different flavors for the e-cigarette 610. In addition, although the e-cigarette 610 is shown as accommodating two cartridges 630A, 630B, it will be appreciated that some devices may accommodate a larger number of cartridges. Furthermore, although cartridges 630A and 630B are the same size as one another, some devices may accommodate cartridges of differing size. For example, an e-cigarette may accommodate one larger cartridge having a nicotine-based liquid, and one or more small cartridges to provide flavor or other additives as desired.

In some cases, the e-cigarette 610 may be able to accommodate (and operate with) a variable number of cartridges. For example, there may be a spring or other resilient device mounted on control unit engagement end 621, which tries to extend along the longitudinal axis towards the mouthpiece 635. If one of the cartridges shown in FIG. 6 is removed, this spring would therefore help to ensure that the remaining cartridge(s) would be held firmly against the mouthpiece for reliable operation.

If an e-cigarette has multiple cartridges, one option is that these are all activated by a single coil that spans the longitudinal extent of all the cartridges. Alternatively, there may an individual coil 650A, 650B for each respective cartridge 630A, 630B, as illustrated in FIG. 6. A further possibility is that different portions of a single coil may be selectively energized to mimic (emulate) the presence of multiple coils.

If an e-cigarette does have multiple coils for respective cartridges (whether really separate coils, or emulated by different sections of a single larger coil), then activation of the e-cigarette (such as by detecting airflow from an inhalation and/or by a user pressing a button) may energize all coils. The e-cigarettes 410, 510, 610 however support selective activation of the multiple coils, whereby a user can choose or specify which coil(s) to activate. For example, e-cigarette 610 may have a mode or user setting in which in response to an activation, only coil 650A is energized, but not coil 650B. This would then produce a vapor based on the liquid formulation in coil 650A, but not coil 650B. This would allow a user greater flexibility in the operation of e-cigarette 610, in terms of the vapor provided for any given inhalation (but without a user having to physically remove or insert different cartridges just for that particular inhalation).

It will be appreciated that the various implementations of e-cigarette 410, 510 and 610 shown in FIGS. 4-6 are provided as examples only, and are not intended to be exhaustive. For example, the cartridge design shown in FIG. 5 might be incorporated into a multiple cartridge device such as shown in FIG. 6. The skilled person will be aware of many other variations that can be achieved, for example, by mixing and matching different features from different implementations, and more generally by adding, replacing and/or removing features as appropriate.

Figure 7:
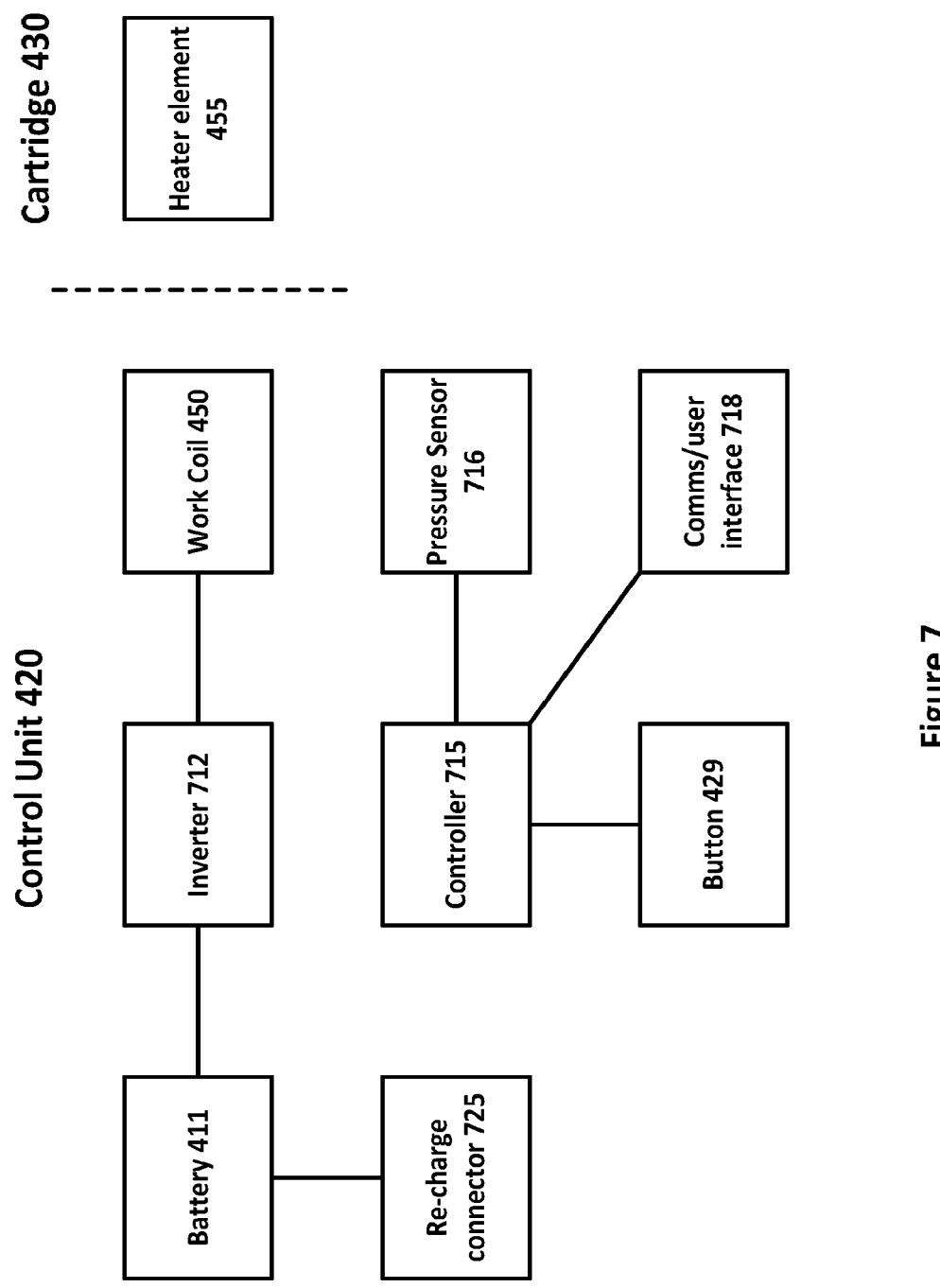
FIG. 7 is a schematic diagram of the control electronics for an e-cigarette such as shown in FIGS. 4, 5 and 6 in accordance with some embodiments of the disclosure.

FIG. 7 is a schematic diagram of the main electronic components of the e-cigarettes 410, 510, 610 of FIGS. 4-6 in accordance with some embodiments of the disclosure. The heater element 455, which is located in the cartridge 430, may comprise any suitable structure, or combination of structures, for inductive heating. The remaining elements shown in FIG. 7 are located in the control unit 420. It will be appreciated that since the control unit 420 is a re-usable device (in contrast to the cartridge 430 which is a disposable or consumable), it is acceptable to incur one-off costs in relation to production of the control unit 420 which would not be acceptable as repeat costs in relation to the production of the cartridge 430. The components of the control unit 420 may be mounted on circuit board 415, or may be separately accommodated in the control unit 420 to operate in conjunction with the circuit board 415 (if provided), but without being physically mounted on the circuit board 415 itself.

As shown in FIG. 7, the control unit 420 includes a re-chargeable battery 411, which is linked to a re-charge connector or socket 725, such as a micro-USB interface. This connector 725 supports re-charging of battery 411. Alternatively, or additionally, the control unit 420 may also support re-charging of battery 411 by a wireless connection (such as by induction charging).

The control unit 420 further includes a controller 715 (such as a processor or application specific integrated circuit, ASIC), which is linked to a pressure or airflow sensor 716. The controller 420 may activate the induction heating, as discussed in more detail below, in response to the sensor 716 detecting an airflow. In addition, the control unit 420 further includes a button 429, which may also be used to activate the induction heating, as described above.

FIG. 7 also shows a comms/user interface 718 for the e-cigarette. This may comprise one or more facilities according to the particular implementation. For example, the user interface 718 may include one or more lights and/or a speaker to provide output to the user, for example to indicate a malfunction, battery charge status, etc. The interface 718 may also support wireless communications, such as Bluetooth or near field communications (NFC), with an external device, such as a smartphone, laptop, computer, notebook, tablet, etc. The e-cigarette may utilize this comms interface 718 to output information such as device status, usage statistics, etc., to the external device, for ready access by a user. The comms interface 718 may also be utilized to allow the e-cigarette to receive instructions, such as configuration settings entered by the user into the external device. For example, the user interface 718 and controller 715 may be utilized to instruct the e-cigarette to selectively activate different coils 650A, 650B (or portions thereof), as described above. In some cases, the comms interface 718 may use the work coil 450 to act as an antenna for wireless communications.

The controller 715 may be implemented using one or more chips as appropriate. The operations of the controller 715 are generally controlled at least in part by software programs running on the controller 715. Such software programs may be stored in non-volatile memory, such as ROM, which can be integrated into the controller 715 itself, or provided as a separate component (not shown). The controller 715 may access the ROM to load and execute individual software programs as and when required.

The controller 715 controls the inductive heating of the e-cigarette by determining when the device is or is not properly activated—for example, whether an inhalation has been detected, and whether the maximum time period for an inhalation has not yet been exceeded. If the controller 715 determines that the e-cigarette is to be activated for vaping, the controller 715 arranges for the battery 411 to supply power to the inverter 712. The inverter 712 is configured to convert the DC output from the battery 411 into an alternating current signal, typically of relatively high frequency—e.g. 1 MHz (although other frequencies, such as 5 kHz, 20 kHz, 80 KHz, or 300 kHz, or any range defined by two such values, may be used instead). This AC signal is then passed from the inverter to the work coil 450, via suitable impedance matching (not shown in FIG. 7) if so required.

The work coil 450 may be integrated into some form of resonant circuit, such as by combining in parallel with a capacitor (not shown in FIG. 7), with the output of the inverter 712 tuned to the resonant frequency of this resonant circuit. This resonance causes a relatively high current to be generated in work coil 450, which in turn produces a relatively high magnetic field in heater element 455, thereby causing rapid and effective heating of the heater element 455 to produce the desired vapor or aerosol output.

Figure 7A:
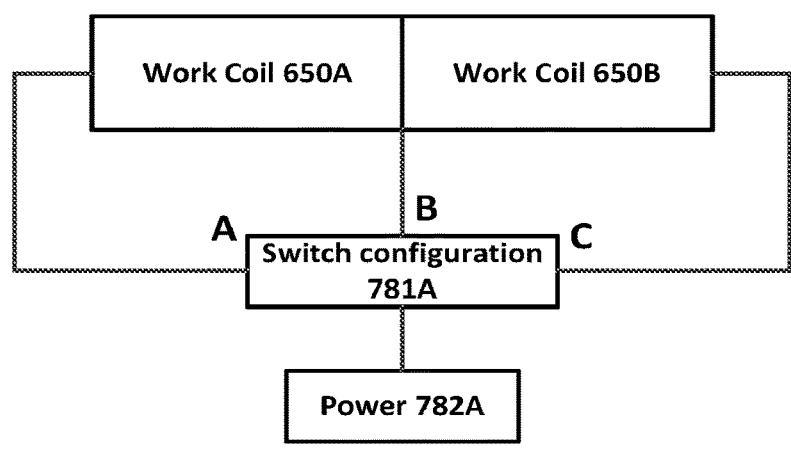
FIGS. 7A, 7B and 7C are schematic diagrams of part of the control electronics for an e-cigarette such as shown in FIG. 6 in accordance with some embodiments of the disclosure.

FIG. 7A illustrates part of the control electronics for an e-cigarette 610 having multiple coils in accordance with some implementations (while omitting for clarity aspects of the control electronics not directly related to the multiple coils). FIG. 7A shows a power source 782A (typically corresponding to the battery 411 and inverter 712 of FIG. 7), a switch configuration 781A, and the two work coils 650A, 650B, each associated with a respective heater element 655A, 655B as shown in FIG. 6 (but not included in FIG. 7A). The switch configuration has three outputs denoted A, B and C in FIG. 7A. It is also assumed that there is a current path between the two work coils 650A, 650B.

In order to operate the induction heating assembly, two out of three of these outputs A, B, C are closed (to permit current flow), while the remaining output stays open (to prevent current flow). Closing outputs A and C activates both coils 650A, 650B, and hence both heater elements 655A, 655B; closing A and B selectively activates just work coil 650A; and closing B and C activates just work coil 650B.

Although it is possible to treat work coils 650A and 650B just as a single overall coil (which is either on or off together), the ability to selectively energize either or both of work coils 650A and 650B, such as provided by the implementation of FIG. 7, has a number of advantages, including:

a) choosing the vapor components (e.g. flavorants) for a given puff. Thus activating just work coil 650A produces vapor just from reservoir 670A; activating just work coil 650B produces vapor just from reservoir 670B; and activating both work coils 650A, 650B produces a combination of vapors from both reservoirs 670A, 670B.

b) controlling the amount of vapor for a given puff. For example, if reservoir 670A and reservoir 670B in fact contain the same liquid, then activating both work coils 650A, 650B can be used to produce a stronger (higher vapor level) puff compared to activating just one work coil by itself.

c) prolonging battery (charge) lifetime. As already discussed, it may be possible to operate the e-cigarette of FIG. 6 when it contains just a single cartridge, e.g. 630B (rather than also including cartridge 630A). In this case, it is more efficient just to energize the work coil 650B corresponding to cartridge 630B, which is then used to vaporize liquid from reservoir 670B. In contrast, if the work coil 650A corresponding to the (missing) cartridge 630A is not energized (because this cartridge 630A and the associated heater element 650A are missing from e-cigarette 610), then this saves power consumption without reducing vapor output.

Although the e-cigarette 610 of FIG. 6 has a separate heater element 655A, 655B for each respective work coil 650A, 650B, in some implementations, different work coils may energize different portions of a single (larger) workpiece or susceptor. Accordingly, in such an e-cigarette 610, the different heater elements 655A, 655B may represent different portions of the larger susceptor, which is shared across different work coils. Additionally (or alternatively), the multiple work coils 650A, 650B may represent different portions of a single overall drive coil, individual portions of which can be selectively energized, as discussed above in relation to FIG. 7A.

If the multiple heater elements are being used to control the amount of vapor for a given puff, then having a larger number of heater elements, e.g. more than the two shown in FIG. 7A, will give a better granularity of control. It will also be appreciated that the vapor amount can be increased by supplying more electrical power to each work coil for energizing the corresponding heater element, however, there are limits on the practicality of this. For example, providing too much power may result in a very high temperature for the heater element, which may alter the chemical constitution of the vapor, as well as presenting a potential safety concern.

Figure 7B:
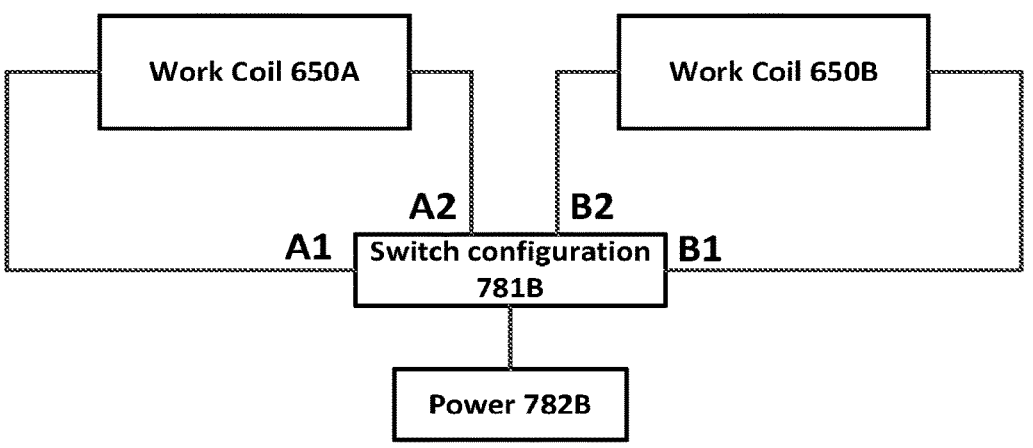

FIG. 7B shows another implementation for supporting selectivity across multiple work coils 650A, 650B. Thus in FIG. 7B, it is assumed that the work coils are not electrically connected to one another, but rather each work coil 650A, 650B is individually (separately) linked to the power source 782B via a pair of independent connections through switch configuration 781B. In particular, work coil 650A is linked to power source 782B via switch connections A1 and A2, and work coil 650B is linked to power source 782B via switch connections B1 and B2. This configuration of FIG. 7B offers similar advantages to those discussed above in relation to FIG. 7A. In addition, the architecture of FIG. 7B may also be readily scaled up to work with more than two work coils.

Figure 7C:
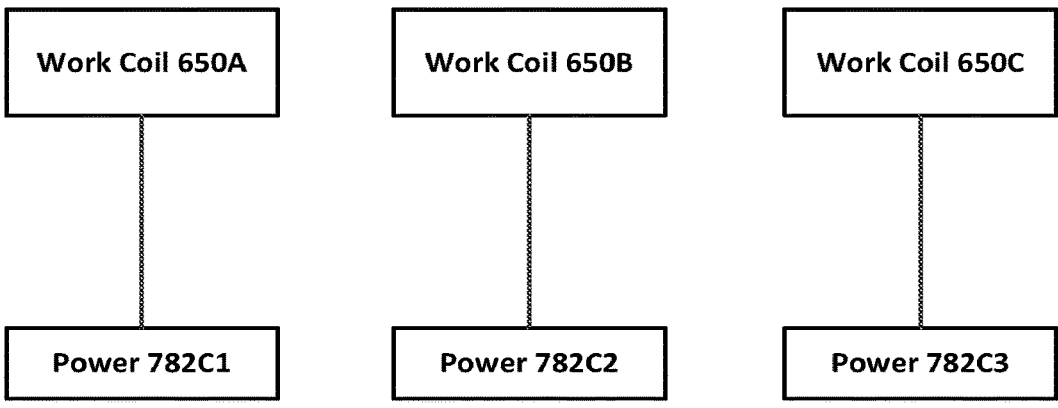

FIG. 7C shows another implementation for supporting selectivity across multiple work coils, in this case three work coils denoted 650A, 650B and 650C. Each work coil 650A, 650B, 650C is directly connected to a respective power supply 782C1, 782C2 and 782C3. The configuration of FIG. 7 may support the selective energization of any single work coil, 650A, 650B, 650C, or of any pair of work coils at the same time, or of all three work coils at the same time.

In the configuration of FIG. 7C, at least some portions of the power supply 782 may be replicated for each of the different work coils 650. For example, each power supply 782C1, 782C2, 782C3 may include its own inverter, but they may share a single, ultimate power source, such as battery 411. In this case, the battery 411 may be connected to the inverters via a switch configuration analogous to that shown in FIG. 7B (but for DC rather than AC current). Alternatively, each respective power line from a power supply 782 to a work coil 650 may be provided with its own individual switch, which can be closed to activate the work coil (or opened to prevent such activation). In this arrangement, the collection of these individual switches across the different lines can be regarded as another form of switch configuration.

There are various ways in which the switching of FIGS. 7A-7C may be managed or controlled. In some cases, the user may operate a mechanical or physical switch that directly sets the switch configuration. For example, e-cigarette 610 may include a switch (not shown in FIG. 6) on the outer housing, whereby cartridge 630A can be activated in one setting, and cartridge 630B can be activated in another setting. A further setting of the switch may allow activation of both cartridges together. Alternatively, the control unit 610 may have a separate button associated with each cartridge, and the user holds down the button for the desired cartridge (or potentially both buttons if both cartridges should be activated). Another possibility is that a button or other input device on the e-cigarette may be used to select a stronger puff (and result in switching on both or all work coils). Such a button may also be used to select the addition of a flavor, and the switching might operate a work coil associated with that flavor-typically in addition to a work coil for the base liquid containing nicotine. The skilled person will be aware of other possible implementations of such switching.

In some e-cigarettes, rather than direct (e.g. mechanical or physical) control of the switch configuration, the user may set the switch configuration via the comms/user interface 718 shown in FIG. 7 (or any other similar facility). For example, this interface may allow a user to specify the use of different flavors or cartridges (and/or different strength levels), and the controller 715 can then set the switch configuration 781 according to this user input.

A further possibility is that the switch configuration may be set automatically. For example, e-cigarette 610 may prevent work coil 650A from being activated if a cartridge is not present in the illustrated location of cartridge 630A. In other words, if no such cartridge is present, then the work coil 650A may not be activated (thereby saving power, etc).

There are various mechanisms available for detecting whether or not a cartridge is present. For example, the control unit 620 may be provided with a switch which is mechanically operated by inserting a cartridge into the relevant position. If there is no cartridge in position, then the switch is set so that the corresponding work coil is not powered. Another approach would be for the control unit 620 to have some optical or electrical facility for detecting whether or not a cartridge is inserted into a given position.

Note that in some devices, once a cartridge has been detected as in position, then the corresponding work coil is always available for activation—e.g. it is always activated in response to a puff (inhalation) detection. In other devices that support both automatic and user-controlled switch configuration, even if a cartridge has been detected as in position, a user setting (or such-like, as discussed above) may then determine whether or not the cartridge is available for activation on any given puff.

Although the control electronics of FIGS. 7A-7C have been described in connection with the use of multiple cartridges, such as shown in FIG. 6, they may also be utilized in respect of a single cartridge that has multiple heater elements. In other words, the control electronics is able to selectively energize one or more of these multiple heater elements within the single cartridge. Such an approach may still offer the benefits discussed above. For example, if the cartridge contains multiple heater elements, but just a single, shared reservoir, or multiple heater elements, each with its own respective reservoir, but all reservoirs containing the same liquid, then energizing more or fewer heater elements provides a way for a user to increase or decrease the amount of vapor provided with a single puff. Similarly, if a single cartridge contains multiple heater elements, each with its own respective reservoir containing a particular liquid, then energizing different heater elements (or combinations thereof) provides a way for a user to selectively consume vapors for different liquids (or combinations thereof).

In some e-cigarettes, the various work coils and their respective heater elements (whether implemented as separate work coils and/or heater elements, or as portions of a larger drive coil and/or susceptor) may all be substantially the same as one another, to provide a homogeneous configuration. Alternatively, a heterogeneous configuration may be utilized. For example, with reference to e-cigarette 610 as shown in FIG. 6, one cartridge 630A may be arranged to heat to a lower temperature than the other cartridge 630B, and/or to provide a lower output of vapor (by providing less heating power). Thus if one cartridge 630A contains the main liquid formulation containing nicotine, while the other cartridge 630B contains a flavorant, it may be desirable for cartridge 630A to output more vapor than cartridge 630B. Also, the operating temperature of each heater element 655 may be arranged according to the liquid(s) to be vaporized. For example, the operating temperature should be high enough to vaporize the relevant liquid(s) of a particular cartridge, but typically not so high as to chemically break down (disassociate) such liquids.

There are various ways of providing different operating characteristics (such as temperature) for different combinations of work coils and heater elements, and thereby produce a heterogeneous configuration as discussed above. For example, the physical parameters of the work coils and/or heater elements may be varied as appropriate—e.g. different sizes, geometry, materials, number of coil turns, etc. Additionally (or alternatively), the operating parameters of the work coils and/or heater elements may be varied, such as by having different AC frequencies and/or different supply currents for the work coils.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein. The disclosure may include other inventions not presently claimed, but which may be claimed in future.

The invention claimed is:

1. An electronic vapour provision system having a longitudinal axis and comprising:
   a control unit and at least one cartridge configured to engage with and disengage from the control unit substantially along said longitudinal axis; and

an induction heating assembly comprising at least one drive coil and at least one heater element, wherein the at least one heater element is located in the at least one cartridge, the at least one cartridge being located, when engaged with the control unit, such that the at least one heater element is within the at least one drive coil,
wherein the electronic vapour provision system is configured to support selective energisation of different portions of the cartridge using the at least one drive coil and the at least one heater element, and
wherein the electronic vapour provision system is configured to support selective energization of a subset of one or more portions of the cartridge from the different portions of the cartridge.

2. The electronic vapour provision system of claim 1, wherein the system supports selective energisation of any individual portion of the cartridge from the different portions of the cartridge.

3. The electronic vapour provision system of claim 1, wherein the system supports energisation of all the portions of the cartridge from the different portions of the cartridge.

4. The electronic vapour provision system of claim 1, wherein there is one drive coil having a plurality of portions, each portion of the drive coil corresponding to a respective portion of the cartridge, and wherein each of the portions of the cartridge may be selectively energised by activating the corresponding portion of the drive coil.

5. The electronic vapour provision system of claim 1, wherein there is a separate drive coil corresponding to each respective portion of the cartridge, and wherein each of the portions of the cartridge may be selectively energised by activating the corresponding drive coil.

6. The electronic vapour provision system of claim 1, wherein the at least one heater element correspond to different portions of a single susceptor, and wherein each portion of the cartridge that can be selectively energised contains a different portion of the single susceptor.

7. The electronic vapour provision system of claim 1, wherein the system has two or three heater elements.

8. The electronic vapour provision system of claim 1, wherein the system has more than three heater elements.

9. The electronic vapour provision system of claim 1, wherein the at least one heater element is located in one cartridge.

10. The electronic vapour provision system of claim 1, further comprising a plurality of cartridges, wherein each cartridge contains a respective heater element.

11. The electronic vapour provision system of claim 7, wherein each of the at least one heater element is a separate susceptor.

12. The electronic vapour provision system claim 1, further comprising a switch configuration located between a battery in the control unit and the at least one drive coil to support selective energisation of different heater elements from the plurality of heater elements.

13. The electronic vapour provision system of claim 12, wherein the setting of the switch configuration to perform selective energisation is set automatically.

14. The electronic vapour provision system of claim 12, wherein a user can directly determine the setting of the switch configuration to perform selective energisation.

15. The electronic vapour provision system of claim 12, wherein the control unit further comprises a user interface or a communications interface for receiving settings information from a user, and wherein the electronic vapour provision system further includes a controller for setting the switch configuration based on the settings information received from the user.

16. The electronic vapour provision system of claim 12, wherein the control unit further comprises a facility for automatically setting the switch configuration based on the presence or absence of a cartridge in the control unit.

17. The electronic vapour provision system of claim 1, wherein the induction heating assembly is configured so that different portions of the cartridge have different operational heating characteristics.

18. The electronic vapour provision system of claim 17, wherein the different operational heating characteristics are at least one of temperature and heating power.

* * * * *